(12) United States Patent
Marinchak

(10) Patent No.: US 11,504,202 B2
(45) Date of Patent: Nov. 22, 2022

(54) MEDICAL DRAPE AND METHODS OF COVERING EQUIPMENT WITH MEDICAL DRAPES

(71) Applicant: Source Surgical, Inc., San Francisco, CA (US)

(72) Inventor: Todd Marinchak, San Francisco, CA (US)

(73) Assignee: Source Surgical, Inc., San Francisco, CA (US)

( * ) Notice: Subject to any disclaimer, the term of this patent is extended or adjusted under 35 U.S.C. 154(b) by 529 days.

(21) Appl. No.: 16/393,614

(22) Filed: Apr. 24, 2019

(65) Prior Publication Data

US 2019/0247134 A1 Aug. 15, 2019

Related U.S. Application Data

(63) Continuation of application No. 14/207,522, filed on Mar. 12, 2014, now Pat. No. 10,285,767.

(Continued)

(51) Int. Cl.
*A61B 46/10* (2016.01)
*A61B 50/30* (2016.01)
*A61B 50/00* (2016.01)

(52) U.S. Cl.
CPC .............. *A61B 46/10* (2016.02); *A61B 50/30* (2016.02); *A61B 2050/0056* (2016.02)

(58) Field of Classification Search
CPC ......... A61B 46/00; A61B 46/10; A61B 46/40; A61B 46/23; A61B 90/50;

(Continued)

(56) References Cited

U.S. PATENT DOCUMENTS 5,178,282 A * 1/1993 Williams .............. A61B 50/30
206/363
5,630,782 A * 5/1997 Adair ................. A61B 1/00073
600/123

(Continued)

FOREIGN PATENT DOCUMENTS

WO  2012078620 A2  6/2012
WO  2014160224 A1  10/2014

OTHER PUBLICATIONS

International Search Authority/U.S., Written Opinion of the International Searching Authority for International Application No. PCT/US2014/026075, titled "Medical drape and methods of covering equipment with medical drapes", dated Jul. 30, 2014.

(Continued)

*Primary Examiner* — Caitlin A Carreiro
(74) *Attorney, Agent, or Firm* — Rimas T. Lukas

(57) ABSTRACT

A sterile drape is provided to cover medical equipment. The drape may include an expandable element to open the open end of the drape. A sheath may also be provided to cover the sheath prior to use. The drape may also be held in a container, which may be coupled to the equipment. Furthermore, the drape may include one or more partially deployed positions in which the drape is partially deployed yet the sterile surface of the drape remains unexposed so that the drape may be partially deployed by non-sterile personnel and stored in a non-sterile area.

18 Claims, 29 Drawing Sheets

Related U.S. Application Data

(60) Provisional application No. 61/785,311, filed on Mar. 14, 2013.

(58) Field of Classification Search
CPC .. A61B 2017/00477; A61B 2050/3008; A61B 50/00; A61B 50/30; A61B 46/20; A61B 46/27; A61B 46/17; A61B 1/00; A61B 1/00135; A61B 1/00145; A61B 2050/005; A61B 2050/0051; A61B 2050/0056; A61B 2050/0067; A61B 2050/0071; A61B 2050/0073; A61B 2050/3009; A61B 2050/3011; A61F 2013/15073
USPC ........ 128/849, 851, 853, 855, 856; 600/101, 600/121–125
See application file for complete search history.

(56) References Cited

U.S. PATENT DOCUMENTS

| | | |
|---|---|---|
| 5,732,712 A | 3/1998 | Adair |
| 5,769,794 A | 6/1998 | Conlan et al. |
| 8,353,880 B1 * | 1/2013 | Pruter ................... A61B 46/10 604/263 |
| 10,285,767 B2 * | 5/2019 | Marinchak ............ A61B 50/30 |
| 2002/0151848 A1 * | 10/2002 | Capote, Jr. ............ A61B 46/10 604/171 |
| 2002/0196906 A1 | 12/2002 | Mun et al. |
| 2008/0144178 A1 | 6/2008 | Dillon et al. |
| 2013/0025605 A1 * | 1/2013 | Ball .................... A61B 6/4423 128/849 |

OTHER PUBLICATIONS

International Search Authority/U.S., International Search Report for International Application No. PCT/US2014/026075, titled "Medical drape and methods of covering equipment with medical drapes", dated Jul. 30, 2014.

International Bureau of WIPO, International Preliminary Report on Patentability, for PCT application No. PCT/US2014/026075, titled "Medical drape and methods of covering equipment with medical drapes", dated Sep. 15, 2015.

* cited by examiner

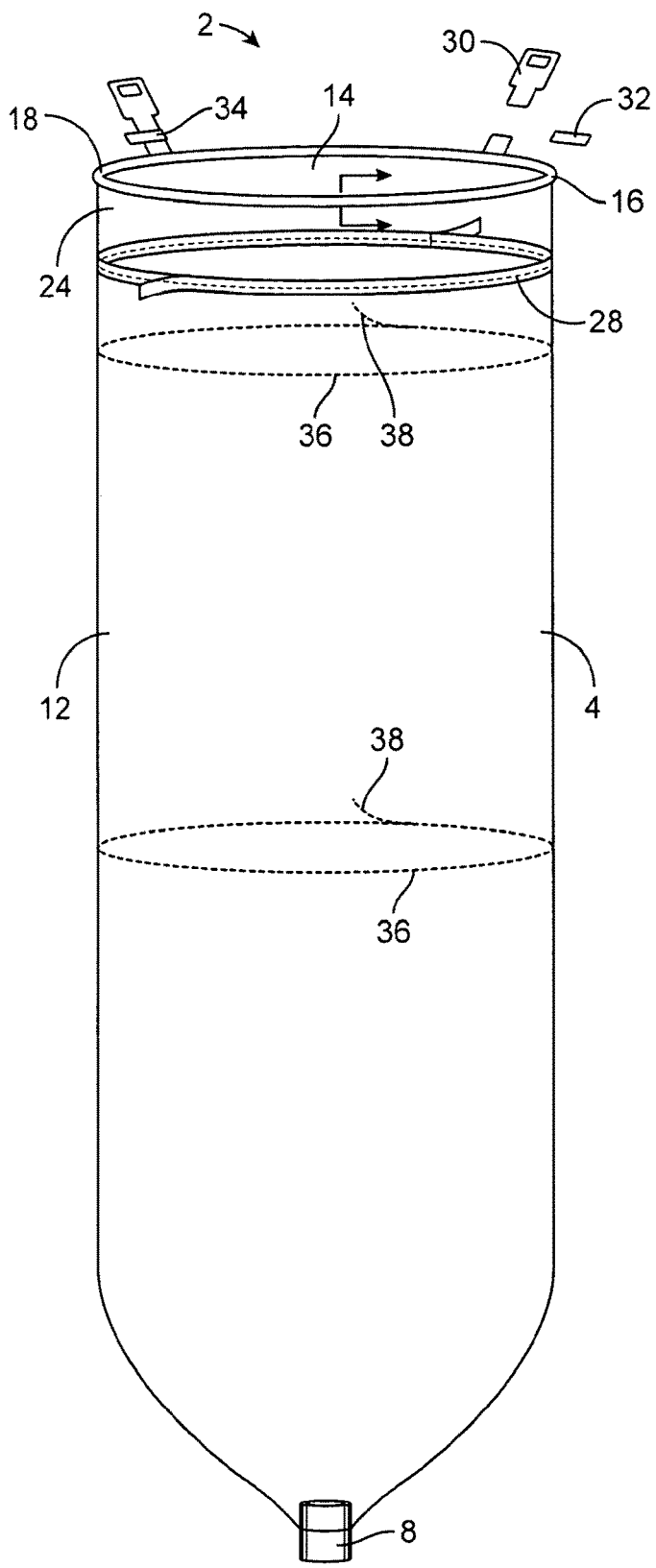
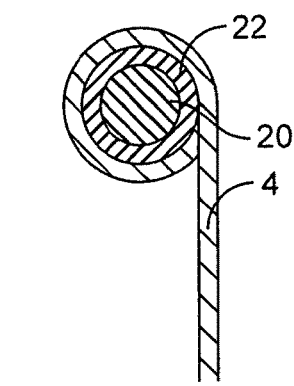
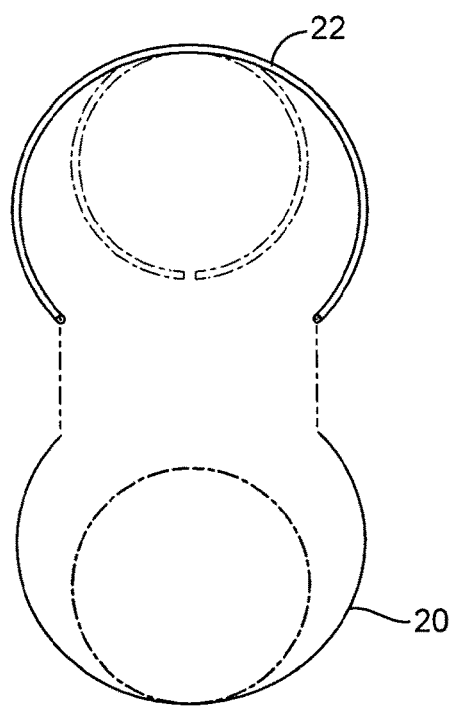
FIG. 1
FIG. 2
FIG. 3

MEDICAL DRAPE AND METHODS OF COVERING EQUIPMENT WITH MEDICAL DRAPES

CROSS-REFERENCE TO RELATED APPLICATION

This application is a continuation of co-pending U.S. patent application Ser. No. 14/207,522 filed on Mar. 12, 2014 entitled "Medical drape and methods of covering equipment with medical drapes" incorporated herein by reference in its entirety which claims priority to and benefit of U.S. Provisional Patent Application Ser. No. 61/785,311 filed on Mar. 14, 2013 incorporated herein by reference in its entirety.

FIELD

The present invention relates to drapes for equipment used in a medical setting. In a specific application, the present invention relates to drapes for large equipment and methods for covering large medical equipment (as opposed to hand-held devices).

BACKGROUND

Equipment used in sterile medical environments (such as a surgery room) must be sterile when entering a sterile field. Small equipment can be readily sterilized between each use or packaged in a sterile manner for single use. Large equipment, such as microscopes, are typically covered with a sterile drape rather than being sterilized after each use since doing so would be impractical.

A conventional method of applying a drape to large equipment, such as a microscope, requires the sterile medical personnel, or another person within the sterile field, to fully deploy the drape during the procedure. The drape is typically a large bag-like structure that is deployed over the equipment in a substantially unfolded state which creates a very unwieldy and awkward deployment since the user must manage the length of the bag while passing the open end of the bag around the equipment. Drapes of this nature may be 4-8 m long.

A problem with the conventional method of deploying a sterile drape over a piece of equipment is that the medical procedure is often delayed since one or more people within the sterile field must deploy the drape. This lengthens the procedure and takes time away from other tasks that could be undertaken.

SUMMARY

The present invention provides a drape that may be deployed over equipment in a non-sterile field thereby freeing up people in the sterile field who would otherwise typically deploy the drape. Moreover, the drape may be deployed while other parts of the procedure are performed since a person not working in the sterile field may deploy the drape of the present invention. These advantages may lead to shorter procedure times and, therefore, reduced cost and increased efficiency.

In one aspect of the invention, the drape is covered by a removable sheath that protects the drape. An advantage of using the removable sheath is that the drape may be deployed and stored in a non-sterile field. The sheath may be removed just prior to the equipment being moved into the sterile field. In this manner, the drape may be partially deployed in advance of any need for the equipment and may be stored in a non-sterile field until needed. The removable sheath may further be sealed to the drape at proximal and/or distal ends of the drape to protect the sterile surfaces prior to removal of the sheath.

The drape and/or the removable sheath may also include an expandable element, which aids in deploying the drape and/or sheath. The expandable element may be a hoop, which is collapsed in a suitable manner. For example, the expandable element may be collapsed into a "figure-8" and even further by folding the figure-8 to align the openings of the figure-8. Alternatively, the expandable element may have a first part slidably coupled to a second part, which permits the expandable element to collapse into a smaller shape when packaged. Of course, the expandable element may be provided in a number of other suitable ways without departing from the scope of the invention including forming a C-shape or U-shape (rather than a complete hoop). Numerous aspects of the present invention may also be practiced without the expandable element.

The proximal end of the drape and/or sheath may also include one or more removable portions, which are removed prior to entering the sterile field. The removable portions are typically those parts, which may be touched or manipulated by the user during deployment of the drape. An advantage of the removable portions is that these parts may be manipulated by non-sterile personnel or come into contact with non-sterile objects as long as they do not touch sterile surfaces and are removed prior to entering the sterile field.

The removable portions may be removed in any suitable manner such as a tear away portion. Of course, the removable portion may be attached with fasteners, a clasp, buttons, a zipper or any other suitable mechanism. The removable portion is removed prior to moving the drape into the sterile field as further described below in connection with use of the drape. For example, the removable handles are removed after use and/or prior to moving the drape into the sterile field. The removable portion advantageously permit parts of the device (specifically non-sterile parts or parts potentially contaminated in a non-sterile field) to be removed prior to moving the equipment into the sterile field.

The drape and/or removable sheath may also include one or more cinches which are used to cinch the drape and/or sheath to the equipment. The cinch may be operated from the radially inner side so that the sterile surfaces are not disturbed and so that the sterile surfaces may remain covered until the equipment is moved into the sterile field.

In still another aspect of the present invention, the drape may be deployed to a partially deployed state. An advantage of the partially deployed state is that the time required to fully deploy the drape is reduced thereby potentially reducing the overall procedure time. In one aspect, the drape is deployed so that at least 25% of the length is deployed and may even be at least 40% of the length. Deployment of these amounts may be preferable when using an everted drape as further described below. When the removable sheath is used, the length of the drape may be at least 80% deployed and may even be completely deployed with only removal of the sheath required to complete deployment of the drape as also described below. Although the drape may be partially deployed in the above described manner, the drape may also be partially deployed by simply coupling the drape to the equipment while the drape is still held by the packaging.

The partially deployed position also advantageously may be provided with the sterile surfaces remaining covered so that the equipment may be stored outside the sterile field while in the partially deployed state. Another advantage is that the removable sheath and/or removable portion of the drape provide parts of the device for non-sterile personnel to use in deploying the drape outside the sterile field with these non-sterile parts being removed prior to moving into the sterile field.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows a drape in accordance with the present invention.

FIG. 2 is a cross-sectional view of the drape and an expandable element which opens the drape.

FIG. 3 shows the expandable element separated from the drape and the two parts of the expandable element separated.

DETAILED DESCRIPTION

Figure 4:
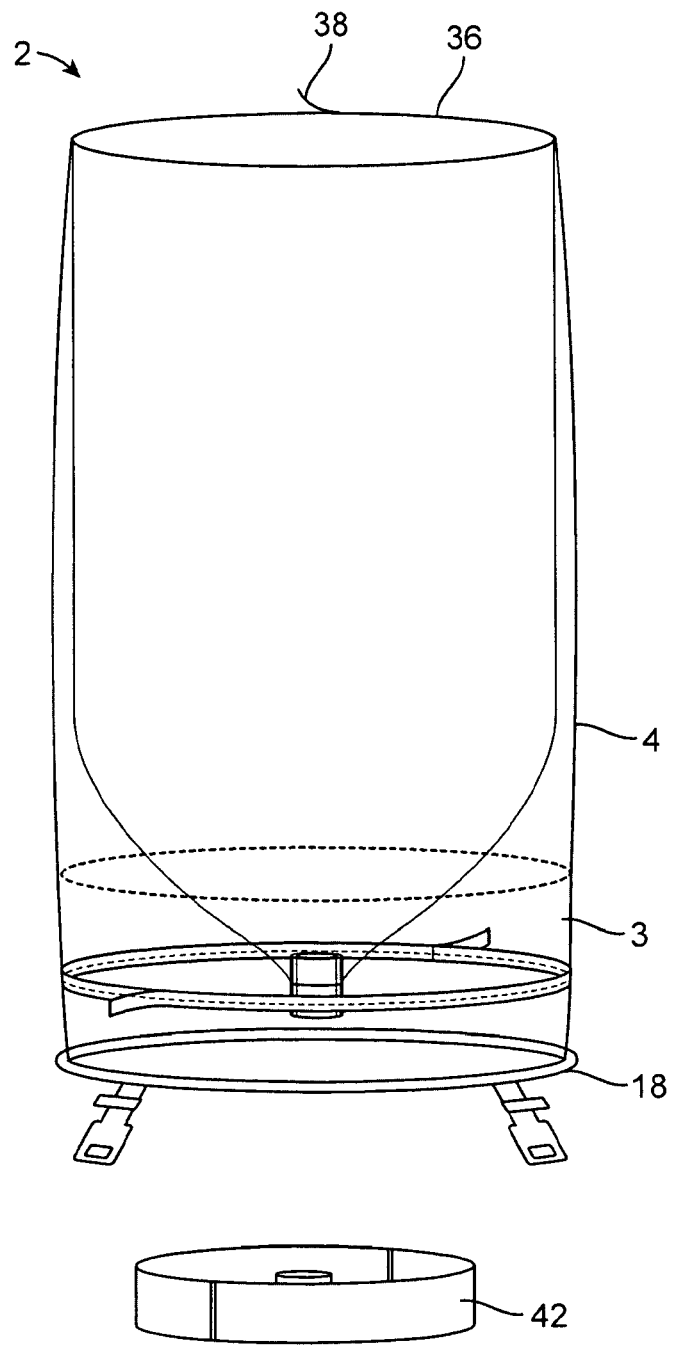
FIG. 4 shows the sidewall of the drape everted in preparation for packaging in the container.

Referring to FIGS. 1-3, 17 and 18, a drape 2 in accordance with the present invention is shown. The drape 2 has a sidewall 4 that forms a flexible bag which covers the equipment 6 as described below. The sidewall 4 is preferably continuous and without openings to prevent exposure of the underlying equipment 6.

The drape 2 has a coupling 8 at a proximal end configured to be coupled to the equipment 6. The coupling 8 may be coupled directly to the equipment 6 or via an adapter 10 (see FIG. 18). The sidewall 4 may be made of any suitable, flexible material including those used for conventional drapes. The sidewall 4 is shown as a simple tube for clarity but may, of course, include various features (protrusions, detents, concave or convex portions) to facilitate manipulating the equipment controls and may take other shapes (such as L-shaped) to generally conform with the shape of the equipment without departing from the scope of the invention.

The sidewall 4 has an outer side 12 which is sterile (together with an external, exposed surface of the coupling 8) thereby providing a sterile barrier over the equipment 6. The equipment 6 may be mounted to a fixed surface (such as the floor, wall or ceiling) using as an arm 13 which may pivot, swivel, telescope or incorporate any other suitable, conventional structure to move the equipment 6. Alternatively, the equipment 6 may be mounted on wheels (not shown) and rolled into the sterile field. As mentioned above, many features of the present invention are directed to applying drapes to relatively large equipment rather than hand held equipment. The equipment may, of course, include a hand-held component attached to a larger piece of equipment without departing from various aspects of the present invention. Furthermore, some features of the present invention may find use with hand-held devices.

The sidewall 4 has an opening 14 at a distal end 16 which is manipulated to deploy the drape 2 over the equipment 6. An expandable element 18 may be provided to open the distal end 16 of the sidewall 4 for use as described below. The expandable element 18 may be formed in any suitable manner. For example, the expandable element 18 may have a first element 20 which telescopes within a second element 22 to expand and collapse the element 18. Each of the elements, 20, 22 is relatively flexible and each may assume the dotted-line shapes of FIG. 3. It is understood that the expandable element 18 may expand and collapse in any suitable manner rather than using the telescoping first and second elements 20, 22. Furthermore, the expandable element 18 does not need to be a completely closed element, for example the expandable element may be C-shaped, V-shaped or U-shaped, without departing from the scope of the invention.

The drape 2 may also have one or more removable portions 24. The removable portions 24, as described below, may be used when manipulating the drape 2 over the equipment 6 and advantageously permits removal after deployment as described below. The removable portion(s) 24 permit the person(s) deploying the drape 2 to be non-sterile, or for some of the deployment of the drape 2 to be conducted outside the sterile field, with the removable portions 24 being removed before moving the equipment 6 into the sterile field.

The removable portion 24 may be bounded by a perforated portion 26 which may be optionally covered with tape 28 to reinforce the perforated portion 26 when the drape 2 is manipulated. Removal of the removable portion 24 also includes removing a portion of the sidewall 4 and the expandable element 18. The removable portion 24 alternatively may be one or more removable handles 30 which are also reinforced with tape 32 or include a tab 34 which is removed to release the handle 30. As mentioned above, the removable portion 24 may be provided in any other suitable manner such as with fasteners, clasp, buttons, zipper or any other suitable mechanism.

The drape 2 may also include one or more cinches 36 to cinch the drape 2 to the equipment 6. Each cinch 36 has an actuator 38 exposed from an inner side 40 of the sidewall 4. The cinches 36 are used as described further below. The cinch 36 may be provided in any suitable manner as is known in the art. The drape 2 may include at least two cinches 36 with one near or at the opening 14 of the sidewall 4 and the other near the midpoint along the length of the drape 2.

Figure 11:
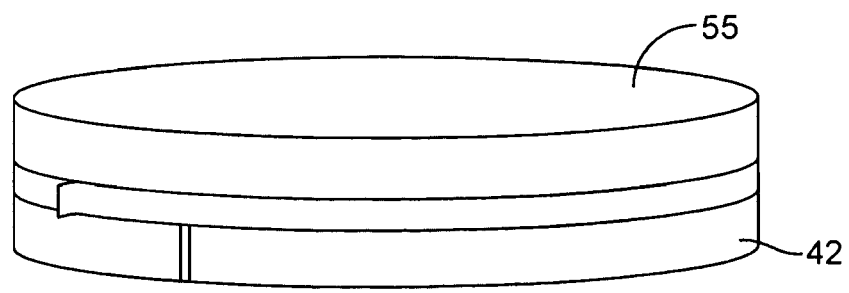
FIG. 11 shows the cover applied to the container.
Figure 12:
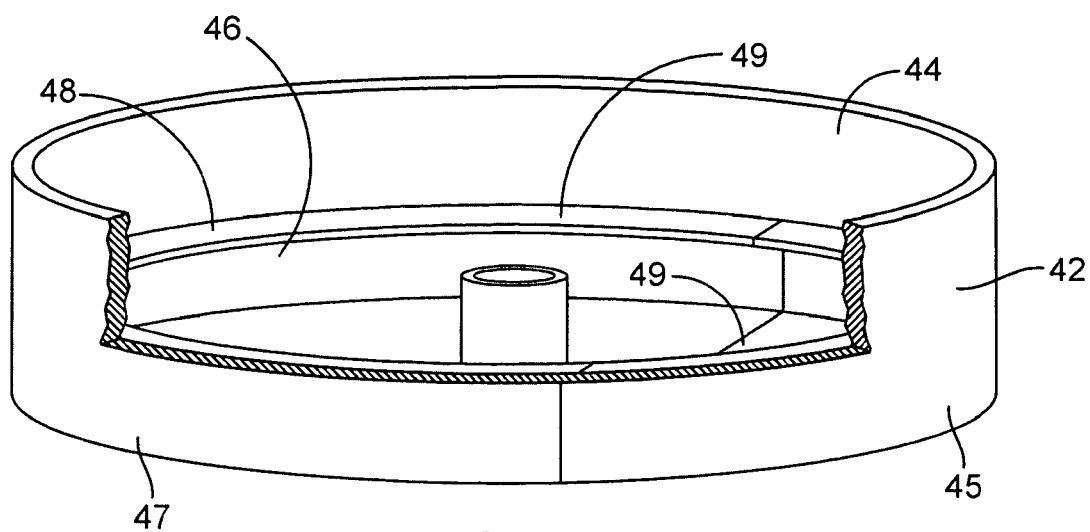
FIG. 12 shows the container.
Figure 13:
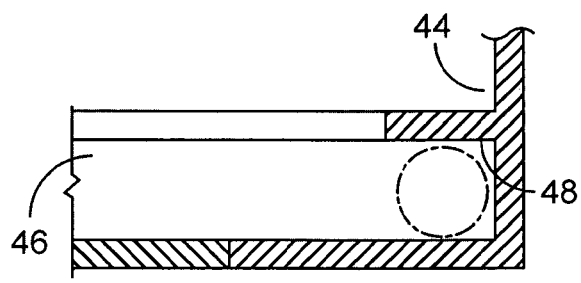
FIG. 13 is a partial cross-sectional view of the container.

Referring now to FIGS. 4-16, the drape 2 is packaged in a container 42 which may hold the expandable element 18 in a collapsed shape. Referring to FIGS. 12-13, the container 42 has a first or upper chamber 44 and a second or lower chamber 46 separated by a divider 48 which may be a circumferential lip 49. The expandable element 18 is positioned in the lower chamber 46 and trapped by the lip 49 to hold the expandable element 18 in the collapsed position as shown in the partial cross-section of FIG. 13.

Figure 5:
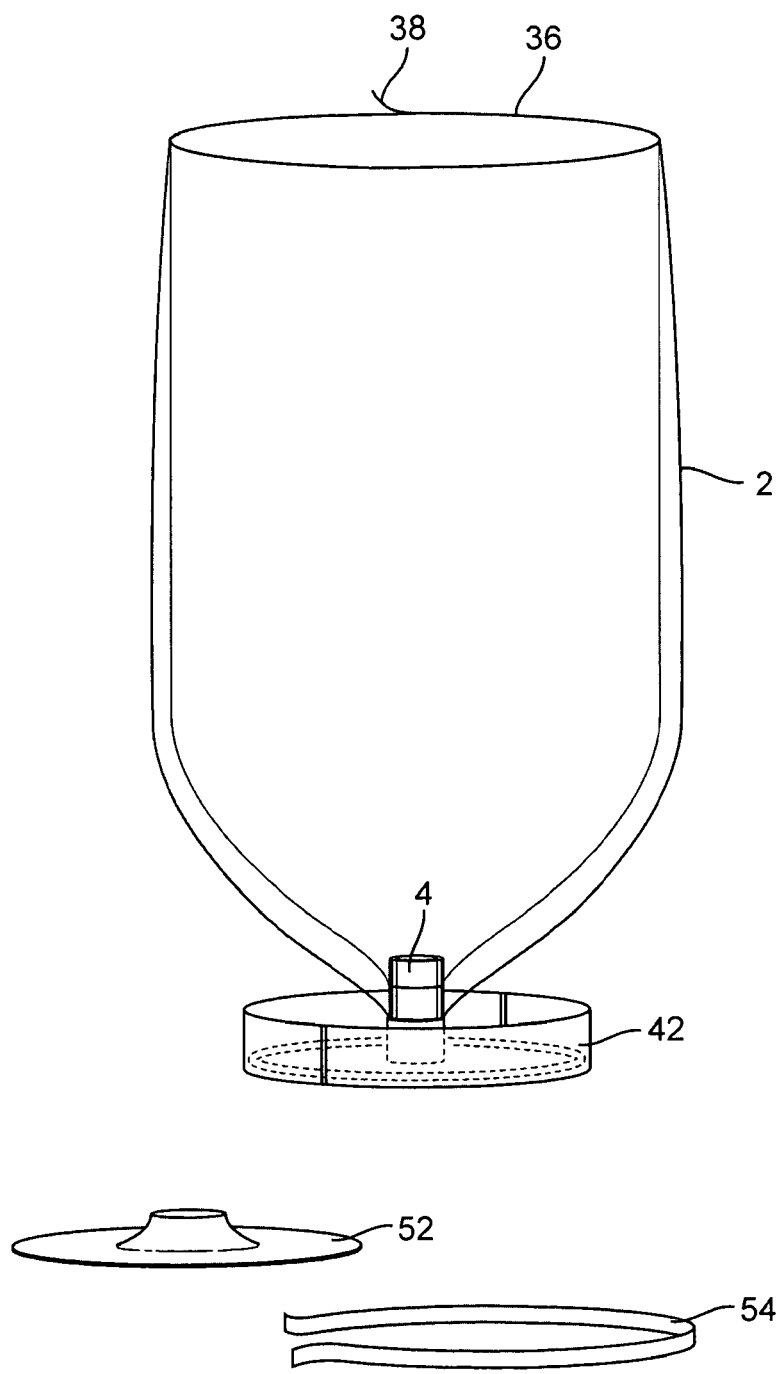
FIG. 5 shows the distal end of the sidewall collapsed and held by the container and a cover and tape used to seal the drape within the container.
Figure 10:
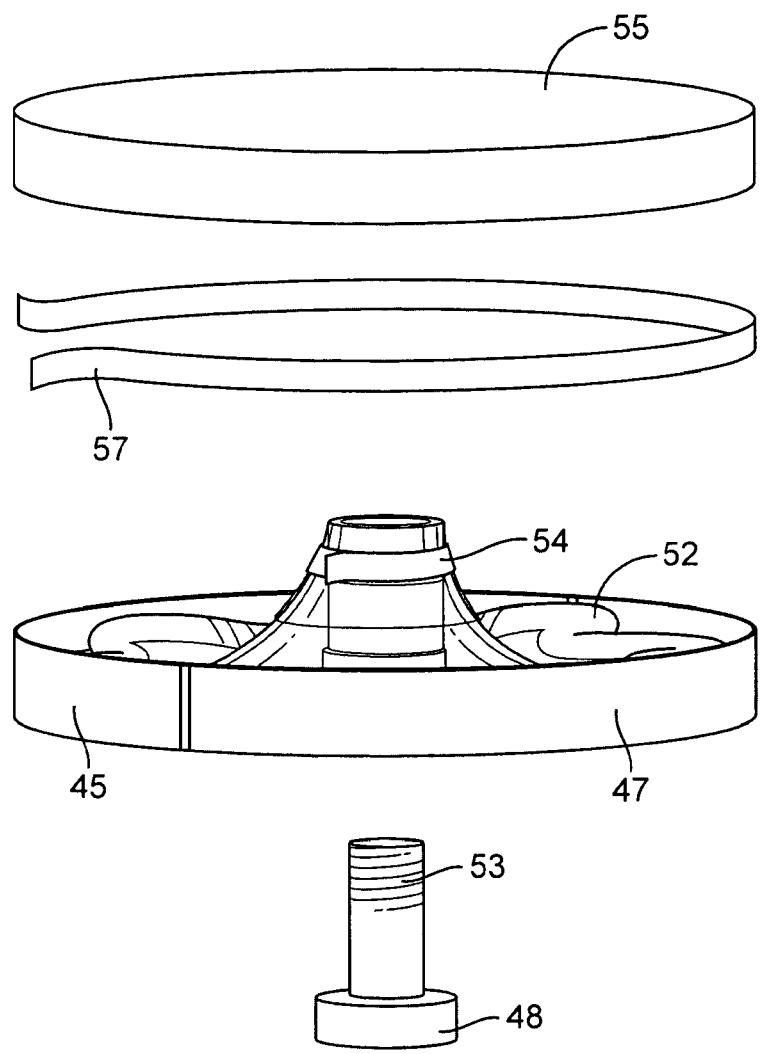
FIG. 10 shows the rolled-up drape with a cover, tape and the actuator prior to completing assembly of the container.

The sidewall 4 is packed and stored in the upper chamber 44 in the manner described below. Referring to FIGS. 5 and 10, a cover 52 is positioned over the drape 2 once the sidewall 4 is packed into the upper chamber 44 and tape 54 may be applied to seal around the coupling 8 while the portion of the coupling 8 that attaches to the piece of equipment 6 remains exposed for use as described below.

Figure 14:
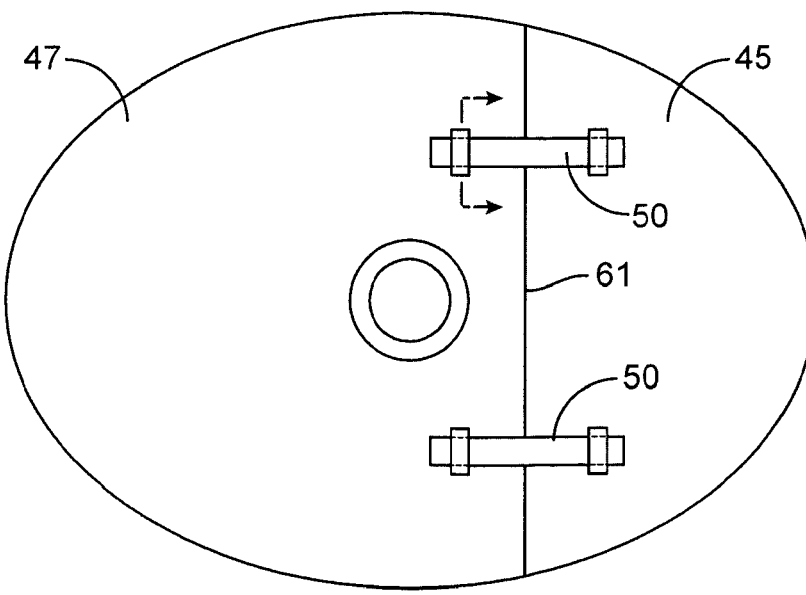
FIG. 14 is a bottom view of the container.
Figure 15:
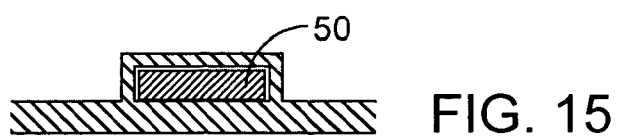
FIG. 15 is a partial cross-sectional view of the container showing the supports which slide within tabs to lock the container in the position of FIG. 12.
Figure 16:
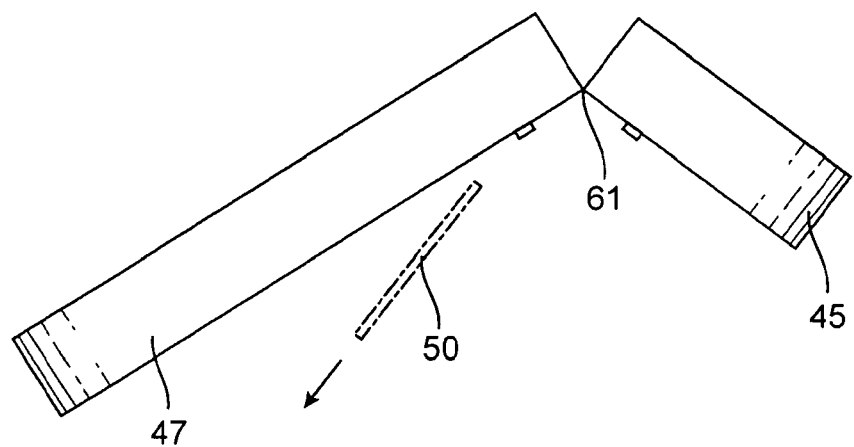
FIG. 16 shows the supports removed to open the container to release the drape.

The container 42 may be formed with a first part 45 connected to a second part 47 with an integrally formed hinged section 61 separating the two parts. Of course, the container 42 may be formed in any other suitable manner to hold the drape 2 and, in particular, maintain the expandable element 18 in the collapsed state. For example, the container 42 may include a soft package suitable sized relative to the expandable element 18 similar to containers that hold collapsible tents. The first and second parts 45, 47 are held in the packaged state of FIG. 12 with supports 50 extending between the first and second parts 45, 47 as shown in FIGS. 14 and 15. Removal of the supports 50 permits the container 42 to open to the position of FIG. 16 thereby permitting release of the drape 2, and particularly the expandable element 18, as described in further detail below.

Referring again to FIGS. 10, 12 and 14, the first part 45 of the container 42 includes a hub 51 through which an actuator 48 extends. The actuator 48 has a threaded portion 53 which engages the coupling 8 thereby securing the coupling 8 to the container 42 as described below. Release of the coupling 8 is achieved by simply rotating the actuator 48 to decouple the drape 2 from the container 42. The actuator 42 may, of course, operate in any other manner such as a frangible portion, a bayonette connection, magnets or any other suitable manner which couples the drape 2 to the container 42 without departing from the present invention. The container 42 also includes a container top 55 (see FIG. 10) that is applied over the first and second parts 45, 47 to seal the drape 2 within the container 42 as shown in FIG. 11.

Before describing use of the drape 2, the procedure for packaging the drape 2 in the container 42 is described to facilitate describing methods of deploying the drape 2. Although the following description provides various methods of packing and deploying the drape 2, the drape 2 may be packed and deployed in various other ways without departing from numerous aspects of the invention. Referring to FIG. 4, a portion of the sidewall 4 is first everted to form an everted portion 3 so that the distal end of the sidewall 4 and the expandable element 18 are positioned proximal to the coupling 8 (sidewall everts from the position of FIG. 1 to FIG. 4). The sidewall 4 may be everted until the cinch 36 near the midpoint of the sidewall 4 is exposed for use as described below. The expandable element 18 is then collapsed and positioned in the lower chamber 46 of the container 42 thereby trapping the expandable element 18 as shown in FIG. 5. A piece of tape 54 may be used to gather the sidewall 4 around the coupling 8.

Figure 6:
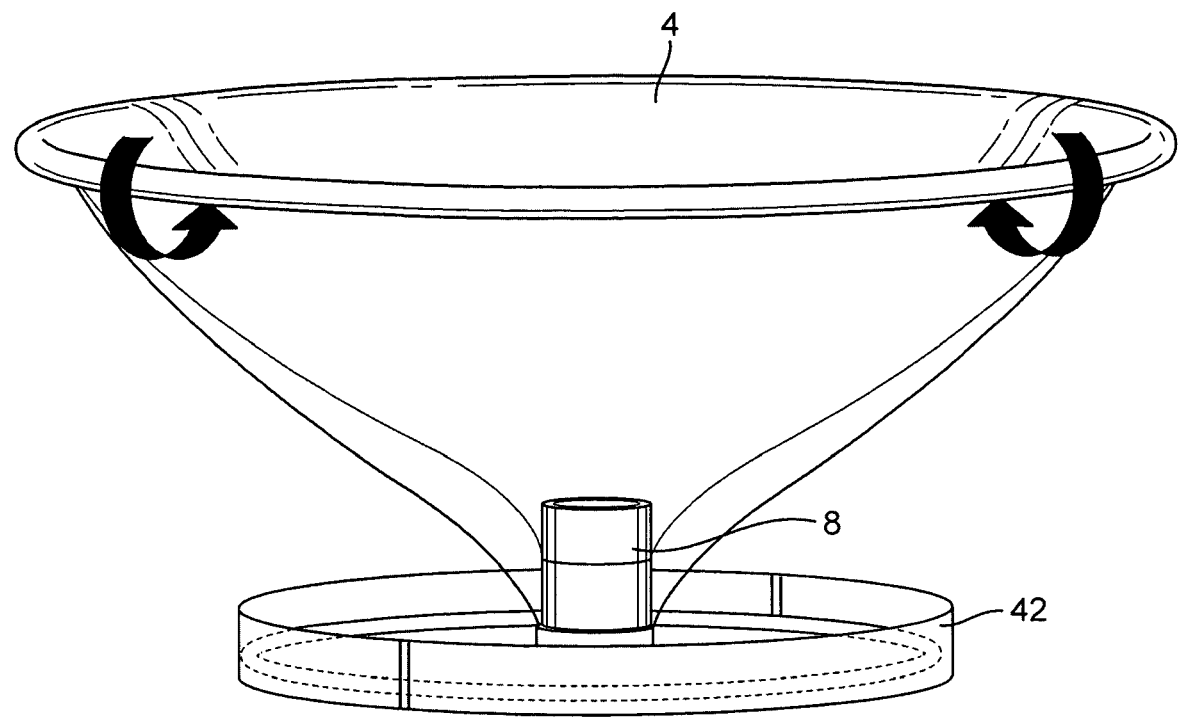
FIG. 6 shows the everted drape rolled-up.
Figure 7:
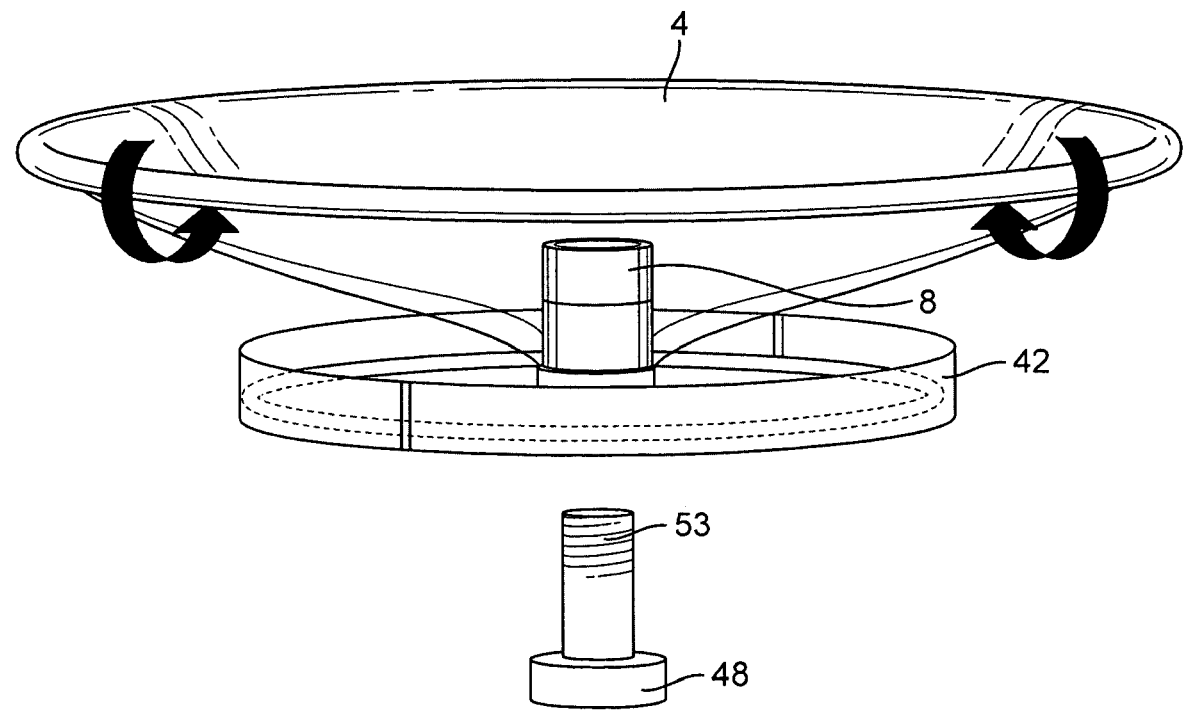
FIG. 7 shows the everted drape rolled up further and an actuator which attaches the container to the coupling of the drape.
Figure 8:
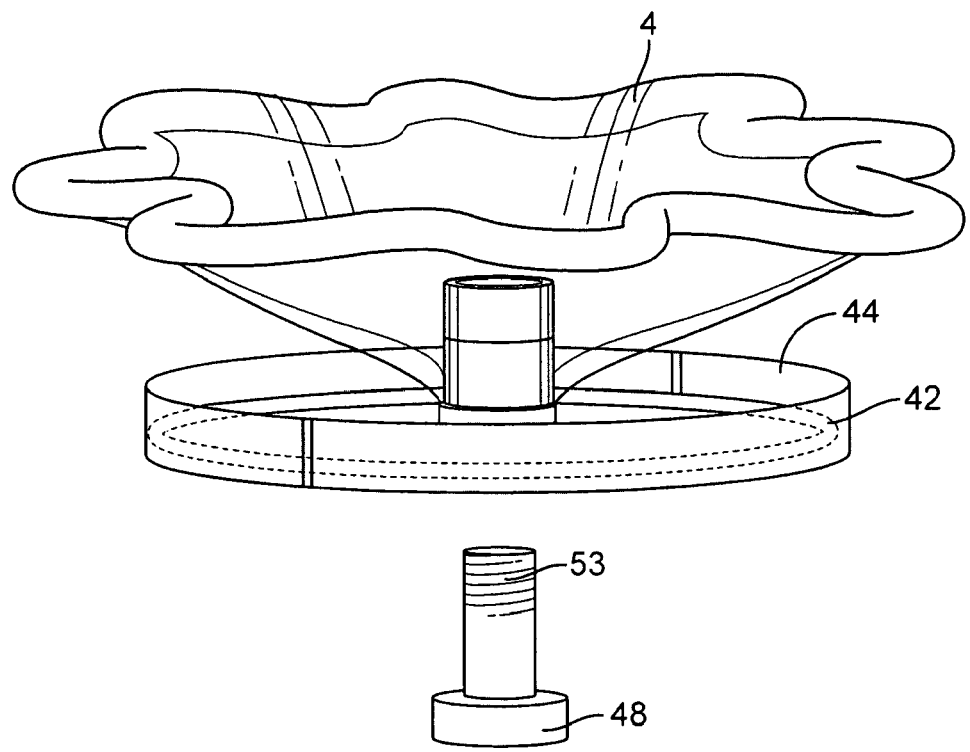
FIG. 8 shows the rolled-up drape folded to reduce the overall size of the rolled-up drape.
Figure 9:
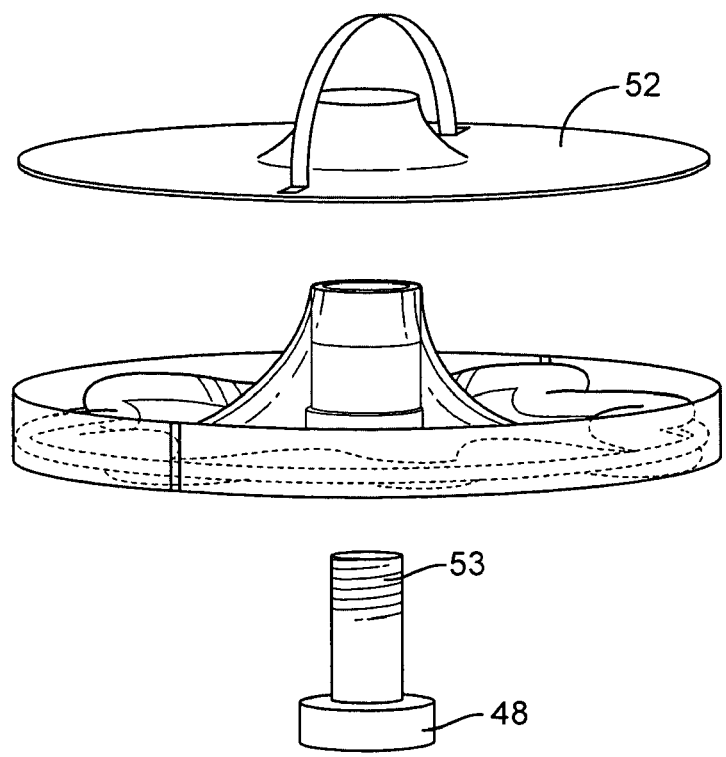
FIG. 9 shows the rolled-up drape placed into an upper chamber of the container.

The everted portion of the sidewall is then rolled-up (together with the other part of the sidewall that is not everted) as shown in FIGS. 6 and 7. The rolled-up sidewall 4 is then folded to reduce the overall size of the sidewall 4 and the sidewall 4 is placed in the upper chamber 44 of the container 42 as shown in FIGS. 8 and 9. The actuator 48 may now be used to attach the coupling 8 to the container 42. The cover 55 and tape 57 are then applied to complete packaging of the drape 2. The container 42 may, of course, be further placed in another sterile package so that the entire container 42 may be used within a sterile setting. Of course, the present invention provides the ability to use the container 42 outside the sterile field as described herein without exposing the sterile outer surface 12.

Use of the drape 2 is now described. In various aspects of the present invention, numerous steps in deployment of the drape 2 may be carried out by non-sterile personnel and/or outside the sterile field. Furthermore, the outer surface 12 of the sidewall 4 (together with other sterile surfaces such as the exposed surface of the coupling 8) are not exposed during early stages of deployment which offers the opportunity to partially deploy the drape 2 and store the equipment 6 in a non-sterile field. In this manner, the time required to complete deployment is reduced once the equipment 6 is needed thereby potentially reducing overall procedure time compared to methods which require full deployment of the drape 2 during the procedure. The drape 2 of the present invention may, in fact, be partially deployed well in advance of the procedure.

The coupling 8 may be coupled directly to the equipment 6 (FIG. 17) or may be coupled to the equipment 6 via the adapter 10 (FIG. 18) in any suitable manner. For example, the coupling 8 may have internal threads 60 (FIG. 10) which mate with a threaded portion on the adapter 10 or on the equipment 6. To engage the coupling 8 with the equipment 6 using the threads 60, the entire container 42 is simply rotated to engage the coupling 8 with the equipment 6 or adapter 10.

Figure 17:
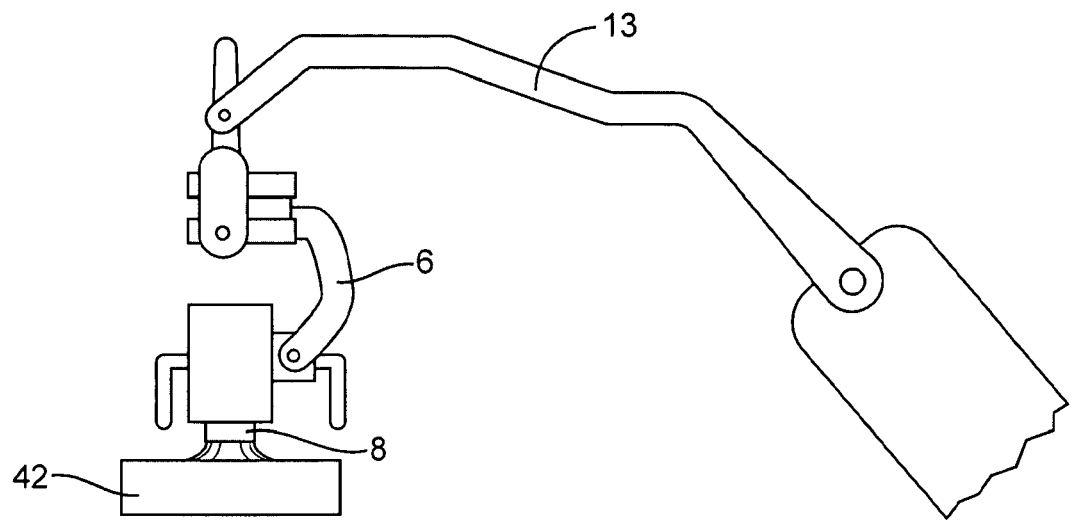
FIG. 17 shows a piece of equipment with the coupling directly attached to the equipment.

Referring to FIG. 17, the sterile surfaces 12 of the drape 2 are not exposed and the container 42 is completely supported by the equipment 6. The expandable element 18 is also held in the collapsed state by the container 42. In one aspect of the present invention, the drape 2 is now in a partially deployed position and may be stored in a non-sterile field.

Figure 18:
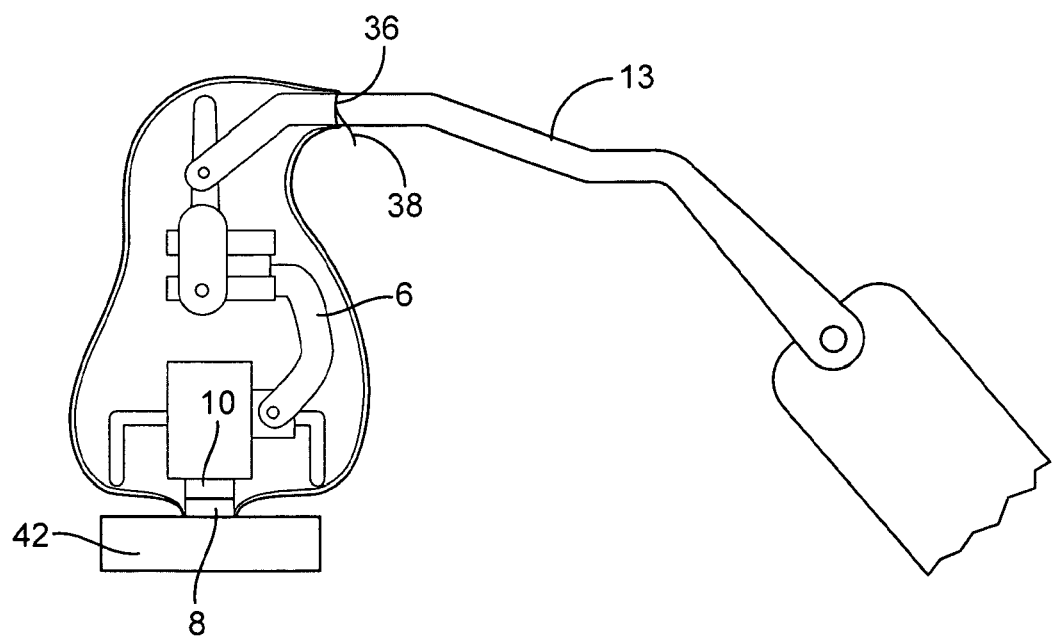
FIG. 18 shows the drape in a partially deployed state and cinched around the equipment, the drape also being coupled to the equipment via an adapter.

The drape 2 may be further deployed without exposing the sterile surfaces 12 as now described. The tape 57 and cover 55 (see FIG. 10) are removed and the sidewall 4 is removed from the container 42 and the everted portion 3 of the sidewall 4 is unrolled to the position of FIG. 18. At this time, the cinch 36 may also be used to gather the sidewall 4 around the equipment 6. As mentioned above, one advantage of the present invention is that the drape 2 may be partially deployed without exposing the sterile surfaces 12 so that the equipment 6 may be stored in a non-sterile area and partially deployed by non-sterile personnel. To this end, the drape 2 may be deployed as shown in FIG. 18 so that at least 25% of a length L of the sidewall 4 (see FIG. 1), or even at least 40% of a length L of the sidewall is deployed over the equipment 6. In this position, the container 42 remains coupled to the drape 2 and to the equipment 6 (directly or via the adapter 10). Stated another way, the present invention describes various partially deployed positions in which the sterile surfaces 12 remain unexposed thereby preventing contamination and permitting storage in a non-sterile area. Stated still another way, the drape 2 is deployed in at least two steps; the first step corresponding to the partially deployed position with the drape completely supported by the equipment 6 and the sterile surfaces covered and the second step completing deployment of the drape 2 including exposure of the sterile outer side 12 of the sidewall 4.

Figure 19:
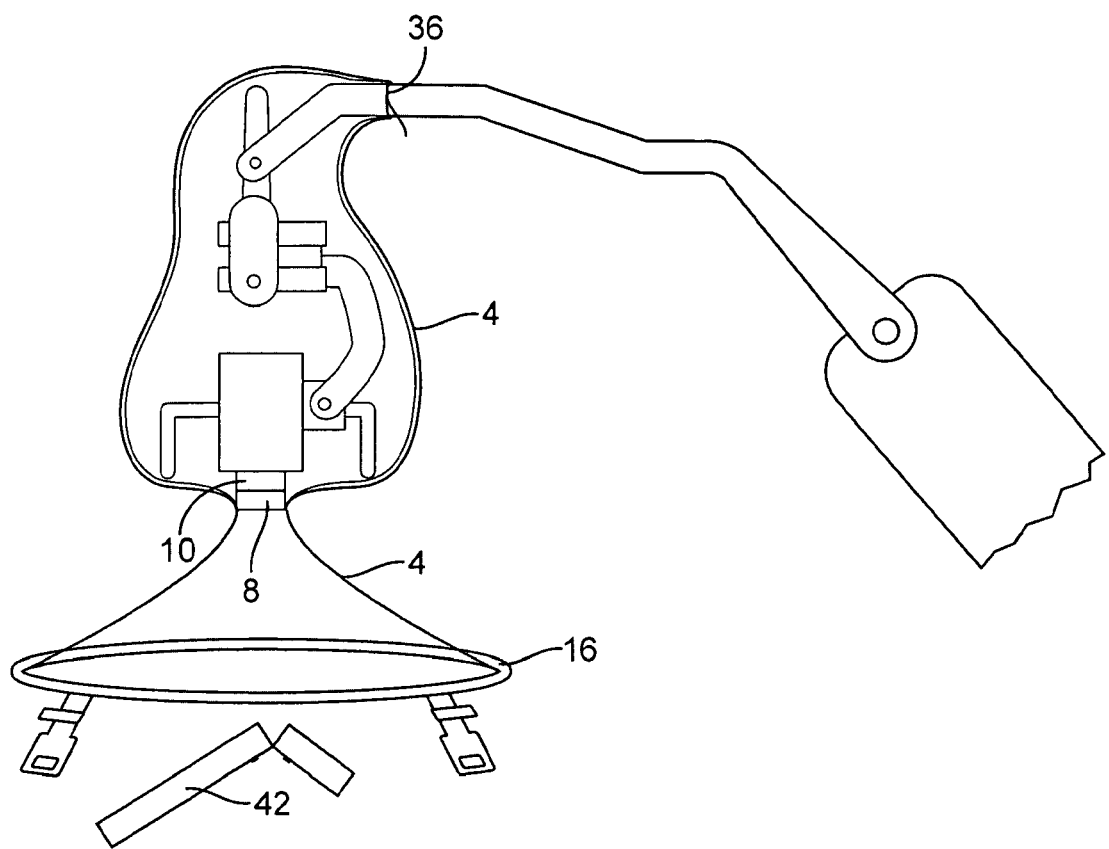
FIG. 19 shows the container removed thereby releasing the expandable element.
Figure 20:
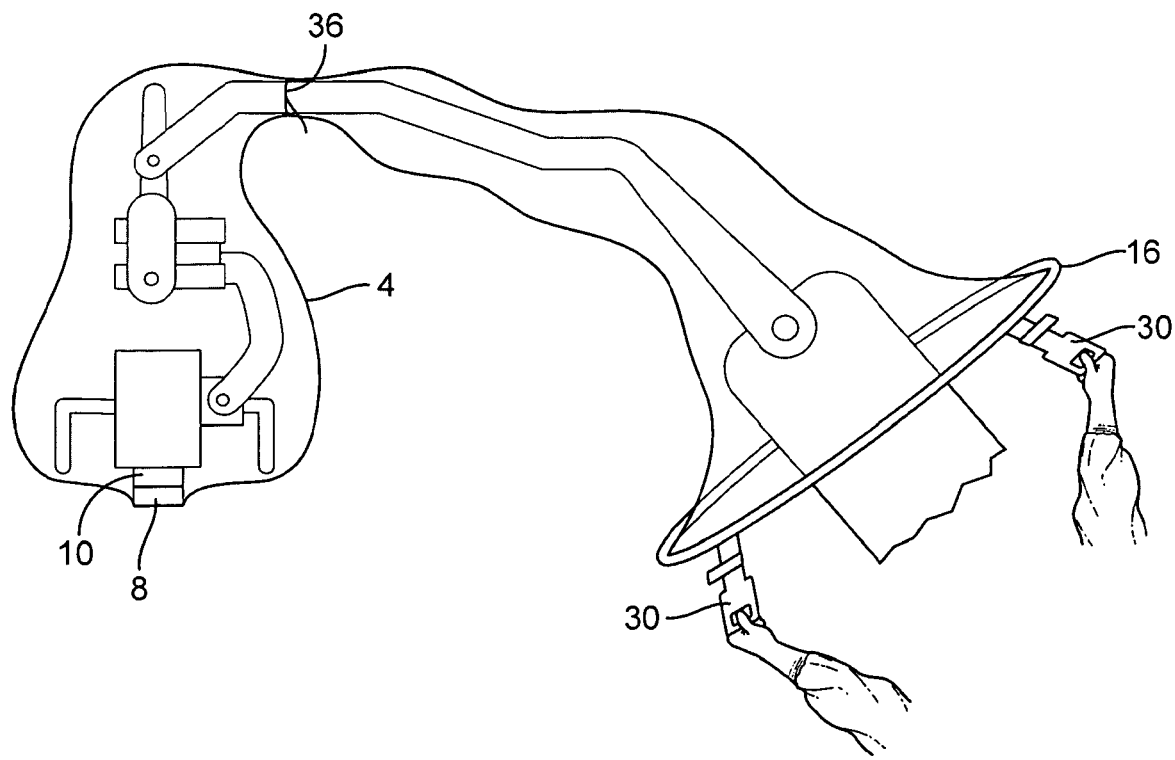
FIG. 20 shows the expandable portion manipulated to deploy the everted portion of the sidewall.
Figure 21:
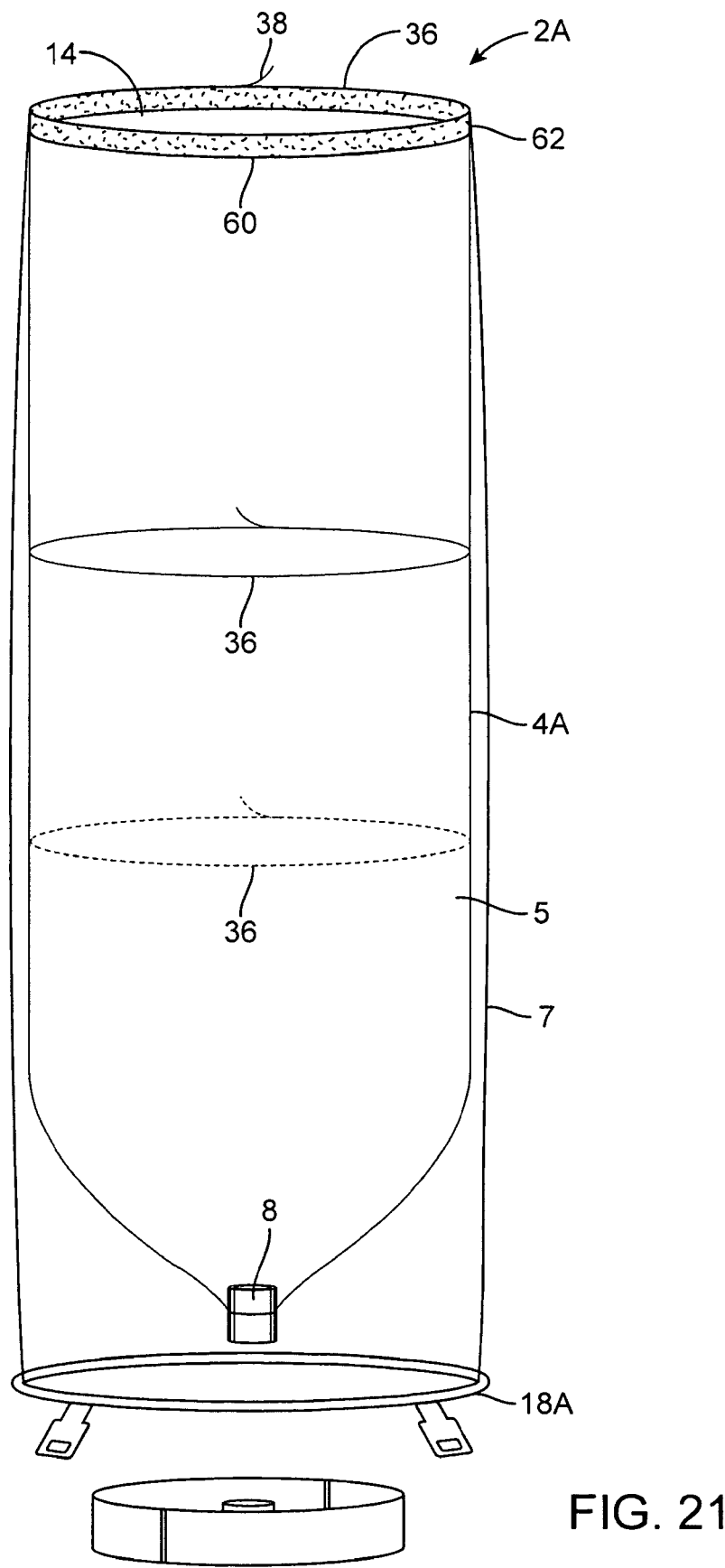
FIG. 21 shows another drape covered by a sheath.

The drape 2 may now be deployed at the appropriate time while being stored in the partially deployed state and in a non-sterile area if desired. When it is desired to move the equipment 6 into the sterile field, the container 42 is opened to release the drape 2 by removing the supports 50 (see FIG. 10) as shown in FIG. 19. The removable portion 24, such as the removable handles 30, are then grasped by one or more people and the everted portion of the sidewall 4 is everted again to deploy the full length of the sidewall 4 as shown in FIG. 20. The removable portion 24, consisting of the removable handles 30 and/or the removable portion of the sidewall 4, may then be removed and the equipment 6 moved into the sterile area at the appropriate time.

Referring now to FIGS. 21-24, another drape 2A is shown with the same or similar reference numbers referring to the same or similar structure. The drape 2A may be deployed in first and second steps and includes one or more partially deployed positions as described above and all methods and relevant aspects of the drape 2 are equally applicable to the drape 2A and incorporated here such as the amount of drape 2A that is deployed in the partially deployed position.

The drape 2A includes the coupling 8, one or more cinches 36, and may include the adapter 10. The drape 2A has a sidewall 4A having a sterile outer surface 12A. A removable sheath 7 covers the sidewall 4A and protects the sterile outer surface 5. An expandable element 18A is coupled to the removable sheath 7 to facilitate removal of the sheath 7 and manipulation of the sheath 7. The expandable element 18A may be the expandable element 18 or any or suitable expandable element. The removable sheath 7 and the sidewall 4A may be bonded to one another with a tear away bond 60 which forms a circumferential seal 62 to protect the sterile surface at the open end 14A of the drape 2A. The drape 2A also includes one or more cinches 36 to gather the drape 2A around the equipment 6.

Packaging of the drape 2A is now described. The expandable element 18A is collapsed and held within the container 42 in the same manner as the expandable member of the drape 2 as shown in FIG. 4. As can be appreciated, the partially everted drape 2 of FIG. 4 forms a similar shape to the drape 2A and sheath 7 of FIG. 21 and, therefore, may be packed similarly. The cover 52 and tape 54 (described in connection with FIG. 5) may be applied over the drape 2A to gather the sheath 7 around the coupling 8. The removable sheath 7 and the sidewall 4A are then rolled up, folded and placed in the upper chamber 45 of the container 42 in the same manner as the procedure of FIGS. 6-9 for the drape 2. Packaging of the drape 2A in the container 42 is then completed in the same manner as the drape 2 and all discussion above is incorporated here.

Use of the drape 2A is now described. Referring again to FIG. 17, the drape 2A may be partially deployed in the same manner as drape 2 with the sidewall 4A still held by the container 42 and the container 42 completely supported by the equipment 6 directly or via the adapter 10. As can be appreciated, even this partially deployed position provides the advantage that the drape 2A is already coupled to the equipment 6 and that the sidewall 4A is ready to be deployed while being held in the container 42.

Figure 22:
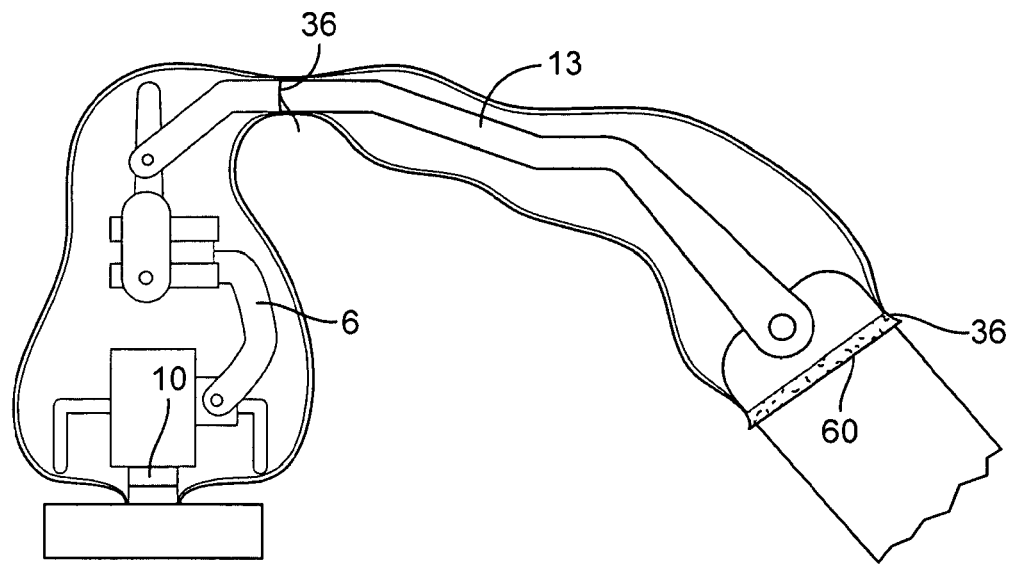
FIG. 22 shows the drape of FIG. 21 partially deployed while the expandable element remains collapsed and sealed within the packaging.
Figure 23:
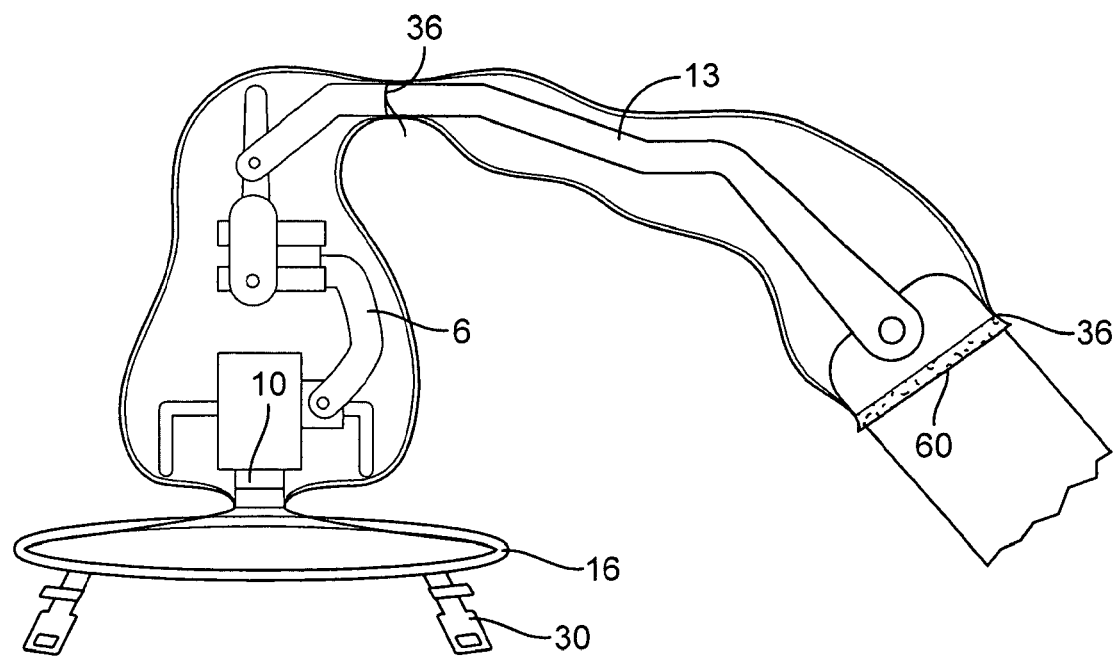
FIG. 23 shows the expandable element released.
Figure 24:
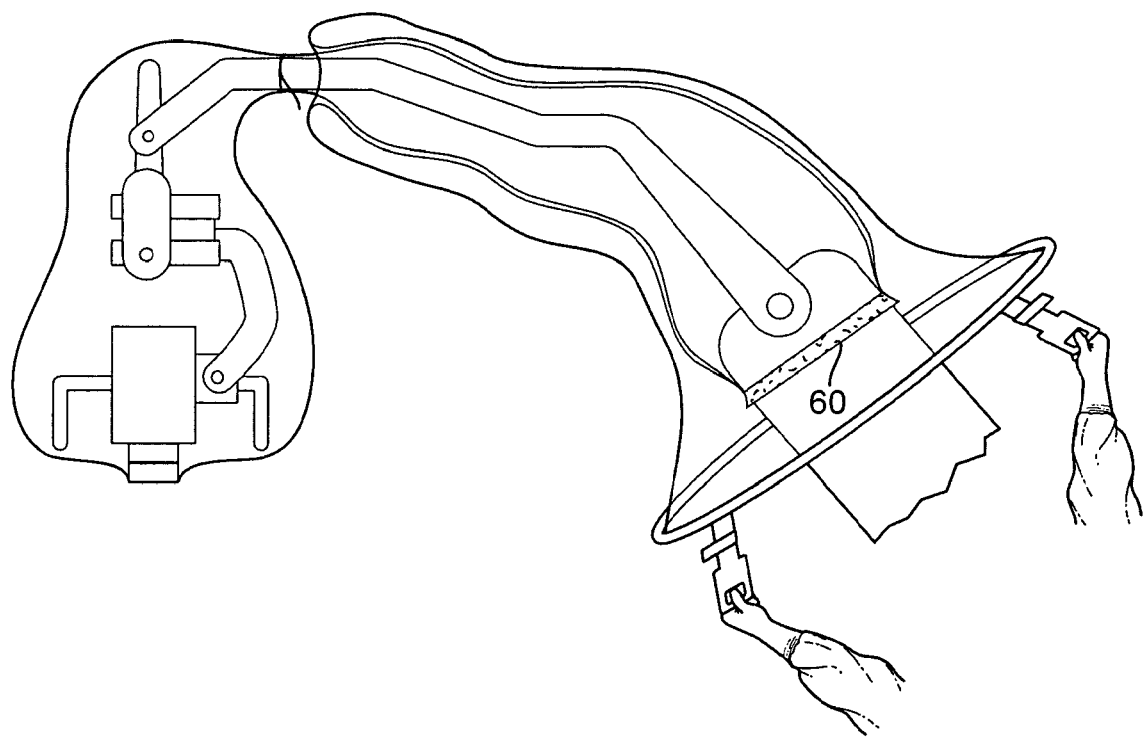
FIG. 24 shows the sheath being removed to expose the sterile drape.

The removable sheath 7 and the sidewall 4A may be further deployed to another partially deployed position as shown in FIG. 22 by unrolling the sheath 7 and sidewall 4A and applying the cinch 36. In this position, the entire length of the sidewall 4A has been deployed while the outer sterile surface 12A remains covered by the removable sheath 7. In this manner, the drape 2A may be stored in a non-sterile location and/or deployed to this point by non-sterile personnel thereby providing the advantages described above. Although the sidewall 4A is fully deployed, the sidewall 4A may be partially deployed, such as at least 80% of the length of the sidewall (or at least 40% or even at least 25% as with the drape 2) without departing from various aspects of the present invention. FIG. 23 shows the container 42 removed which releases the expandable element 16. The handles 30 may then be used to remove the sheath 7 as shown in FIG. 24. The sheath 7 is then completely removed with the sheath 7 separating from the sidewall 4A at the tear away bond 60 (not shown).

Figure 25:
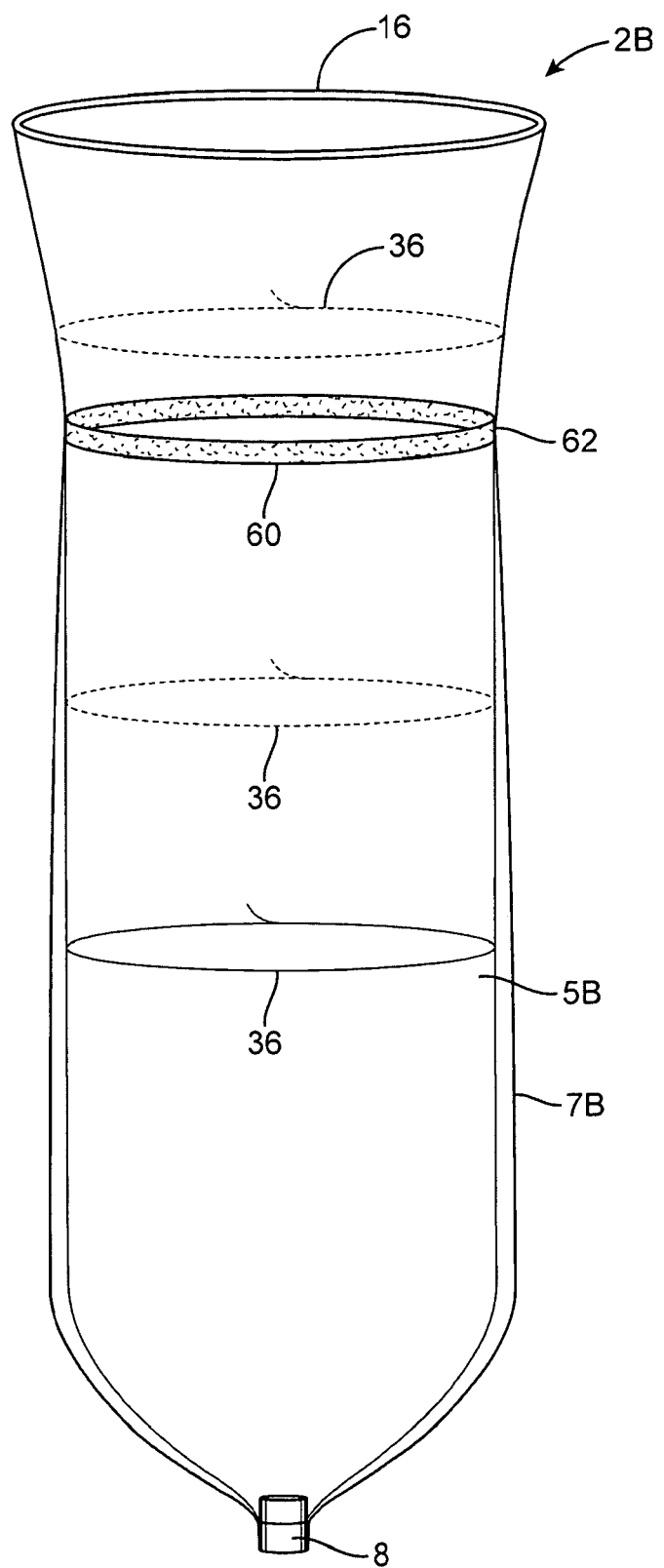
FIG. 25 shows still another drape.

Referring now to FIG. 25, another drape 2B is shown wherein the same or similar reference numbers refer to the same or similar structure. The drape 2B may be deployed in steps and includes a partially deployed position as described above and all methods of using the drape 2, 2A are equally applicable to the drape 2B and are incorporated here including all aspects of the partially deployed position.

Figure 26:
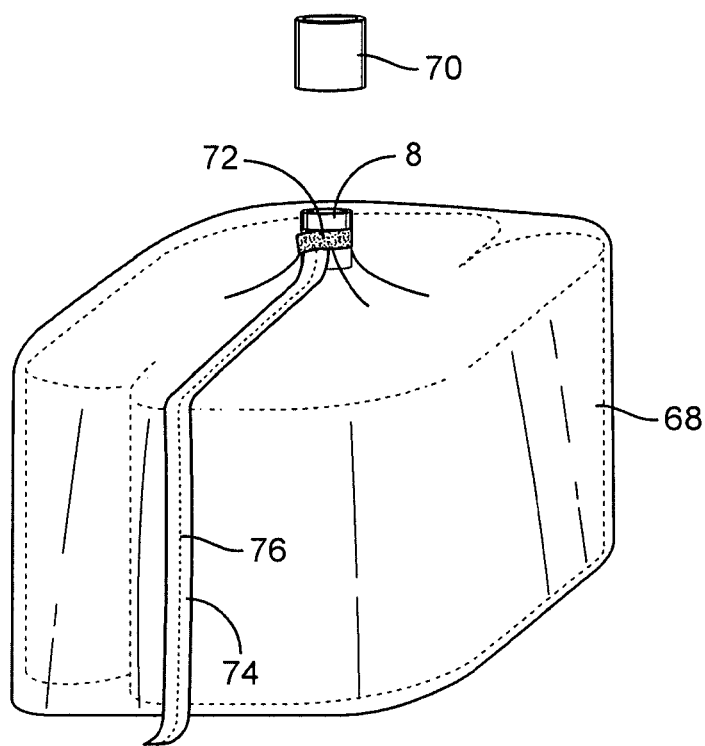
FIG. 26 shows the drape of FIG. 25 contained within a package having a top covering the coupling.
Figure 27:
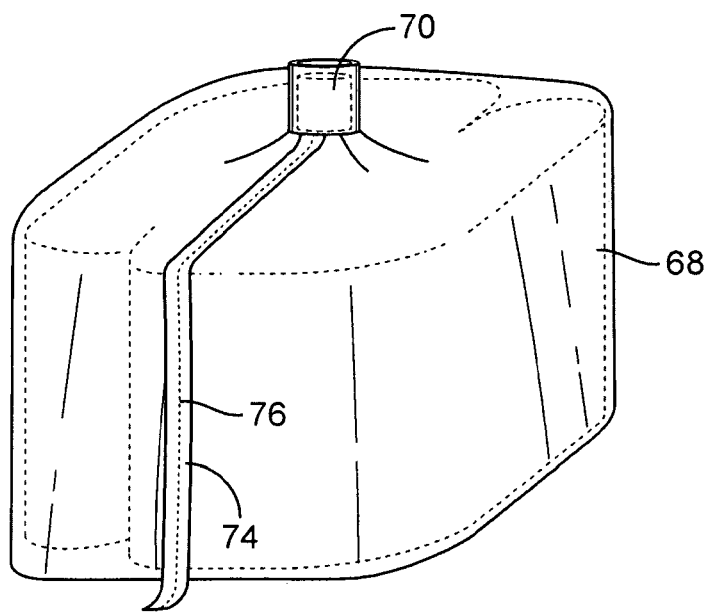
FIG. 27 shows the top covering the coupling.

The drape 2B is contained within a package 68 as shown in FIGS. 26 and 27. A package top 70 covers and seals around the coupling 8. The package 68 is further sealed around the coupling 8 with a piece of tape 72 or with a tear away seal 73 so that the drape 2B remains sealed within the package 68 even when the package top 70 is removed. Another piece of tape 74 covers a perforated section 76 which is used to remove the package 68 completely.

The drape 2B differs from drape 2 and 2A in that a sheath 7B extends over the coupling 8 thereby sealing and protecting the entire drape 2B and the coupling 8 as well. As will be discussed below, the drape 2 and drape 2A may be substituted for drape 2B and used with the container 42 and methods associated therewith. The drape 2B and methods of packaging the drape 2B (as well as drape 2 and drape 2A) are now described.

Figure 28:
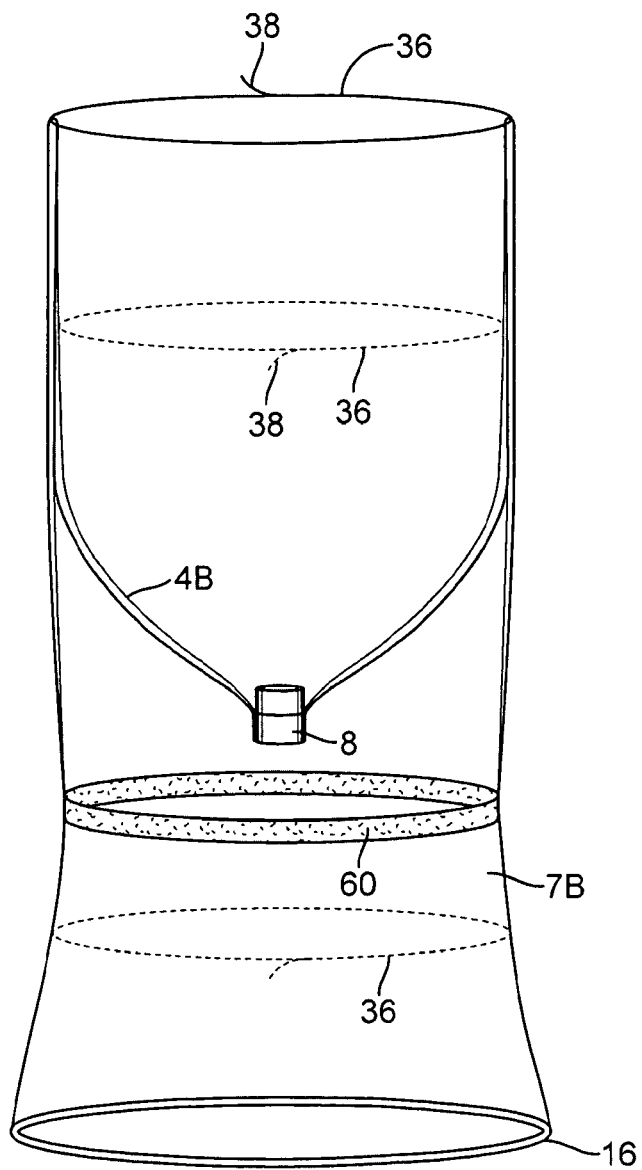
FIG. 28 shows the drape partially everted.
Figure 29:
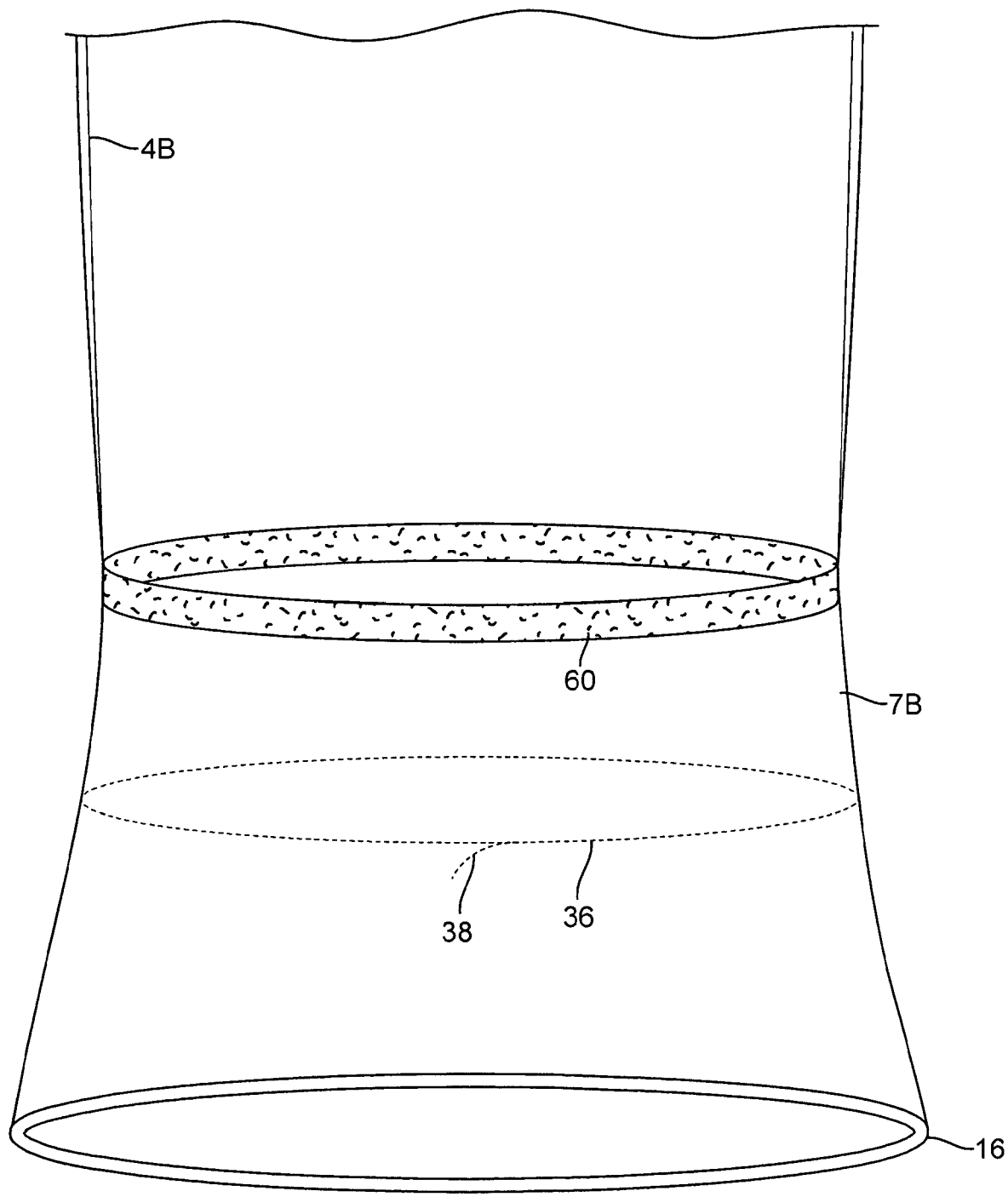
FIG. 29 shows the expandable element of the partially everted drape.
Figure 30:
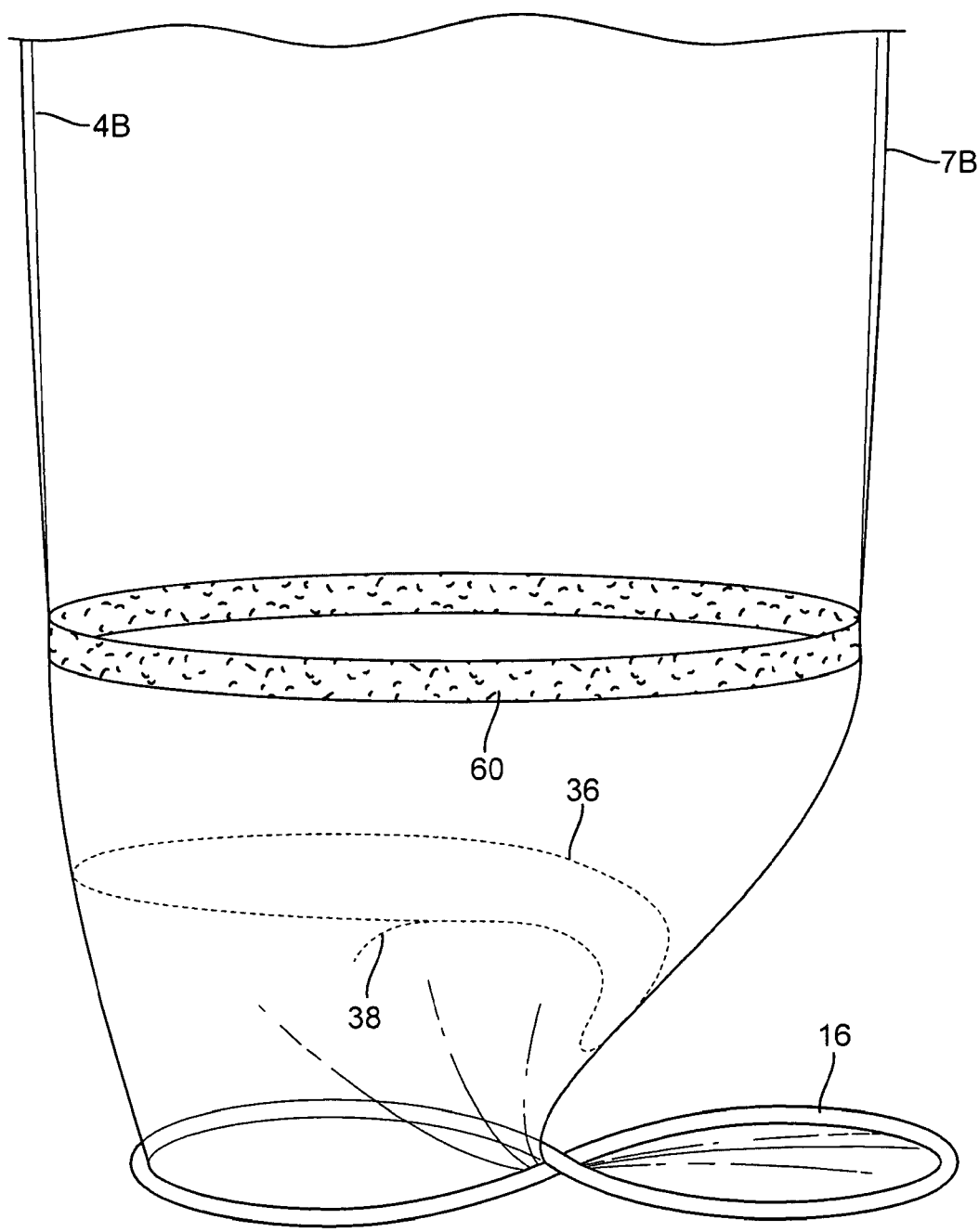
FIG. 30 shows the expandable element folded into a figure 8.
Figure 31:
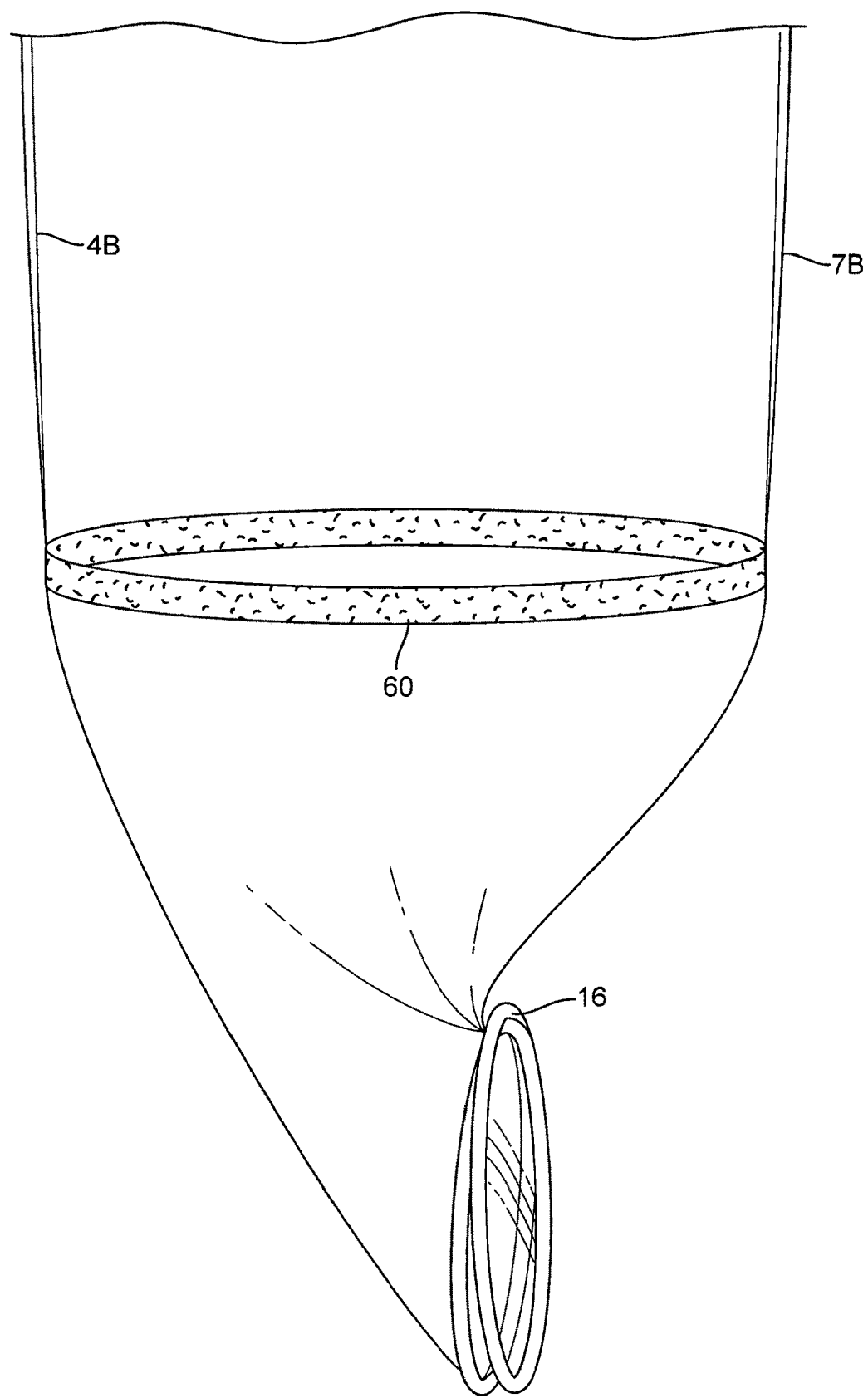
FIG. 31 shows the expandable element further folded to align the openings in the figure 8.
Figure 32:
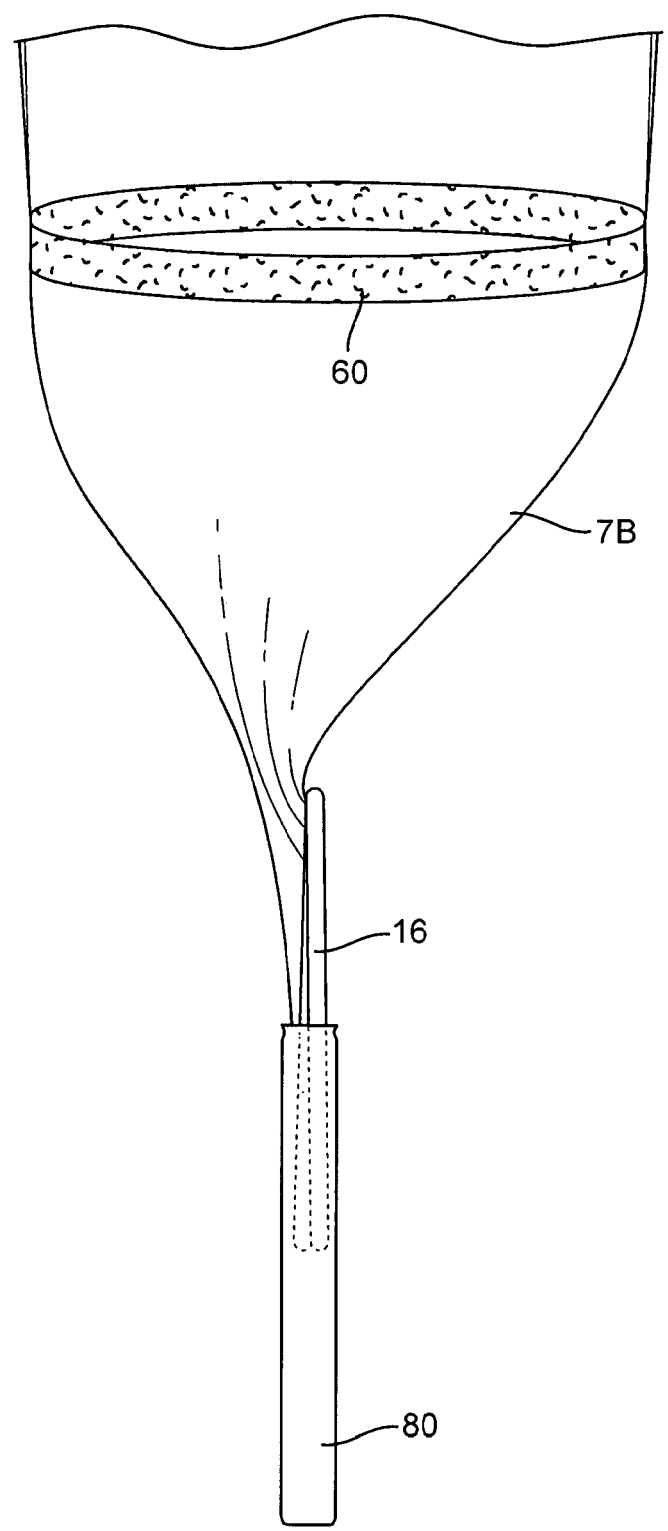
FIG. 32 shows the collapsed expandable element placed into a holder.

The drape 2B is first partially everted as shown in FIG. 28. It can be appreciated that the partially everted drape 2B can be substituted with drape 2 of FIG. 4 or the drape 2A of FIG. 22 and all uses of drape 2 and drape 2A are incorporated here and such substitution is explicitly incorporated here. FIGS. 29-32 show the steps of collapsing the expandable element. First, the expandable element 16 is collapsed to form a figure 8 and the figure 8 is then further collapsed by folding the two sides of the figure 8 together to align openings 79 of the figure 8 as shown in FIG. 31. The expandable element 16 is then placed in a holder 80 that holds the expandable element 16 in the collapsed position. The holder 80 may be a pouch appropriately sized to hold the collapsed element 16 or may simply be one or more clips or other appropriate structure, which holds the collapsed element 16.

Figure 33:
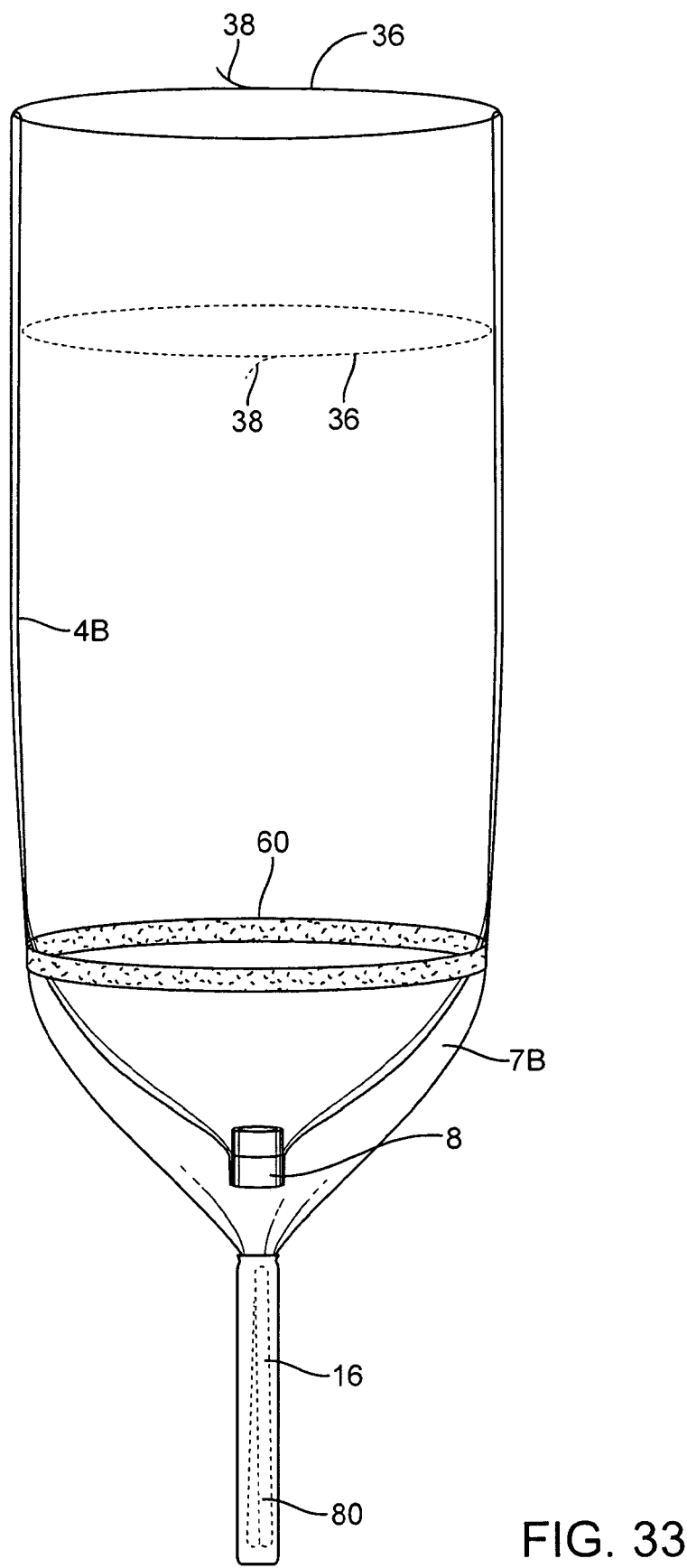
FIG. 33 shows the drape extending out of the holder with the expandable element held by the holder.
Figure 34:
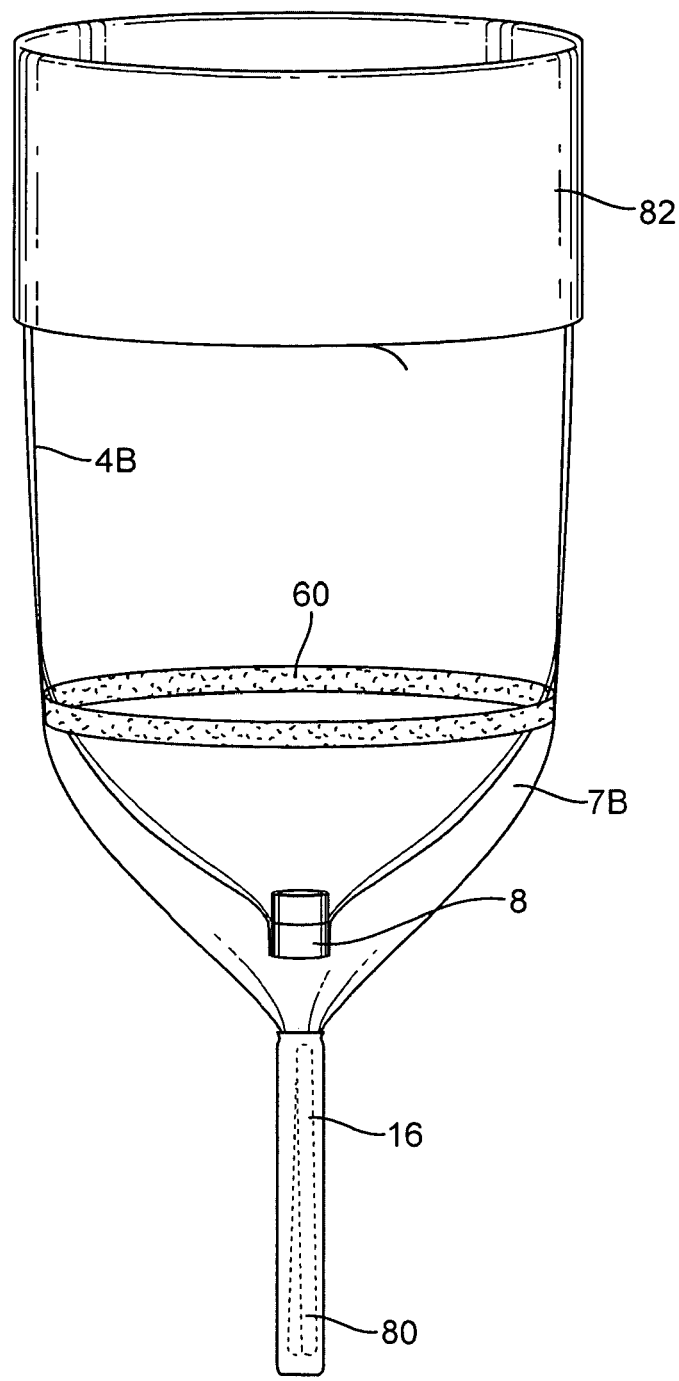
FIG. 34 shows the drape folded down to form a cuff.
Figure 35:
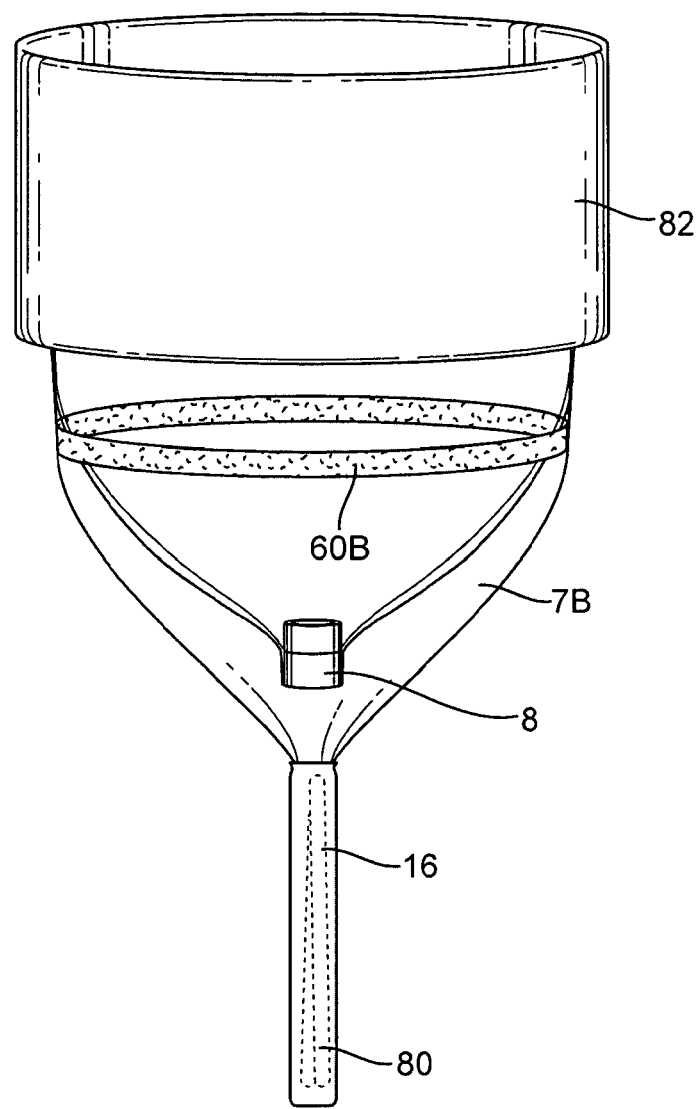
FIG. 35 shows the drape folded further.
Figure 36:
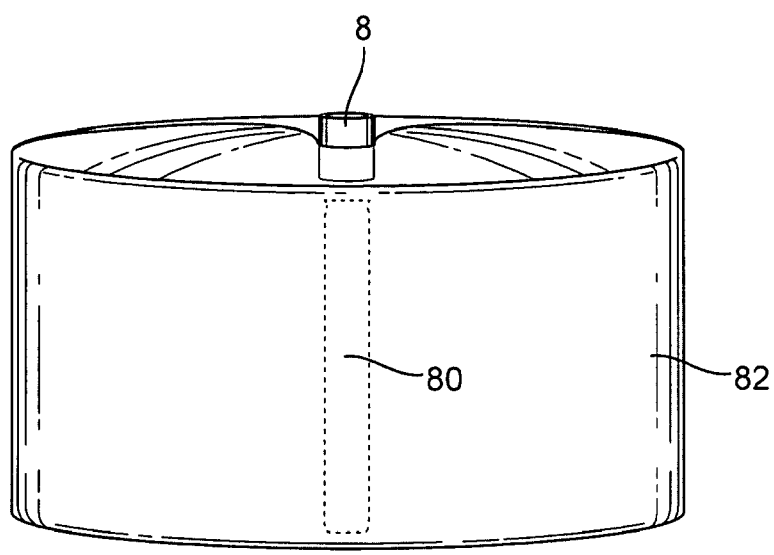
FIG. 36 shows the drape cuffed until the drape is folded around the holder.
Figure 37:
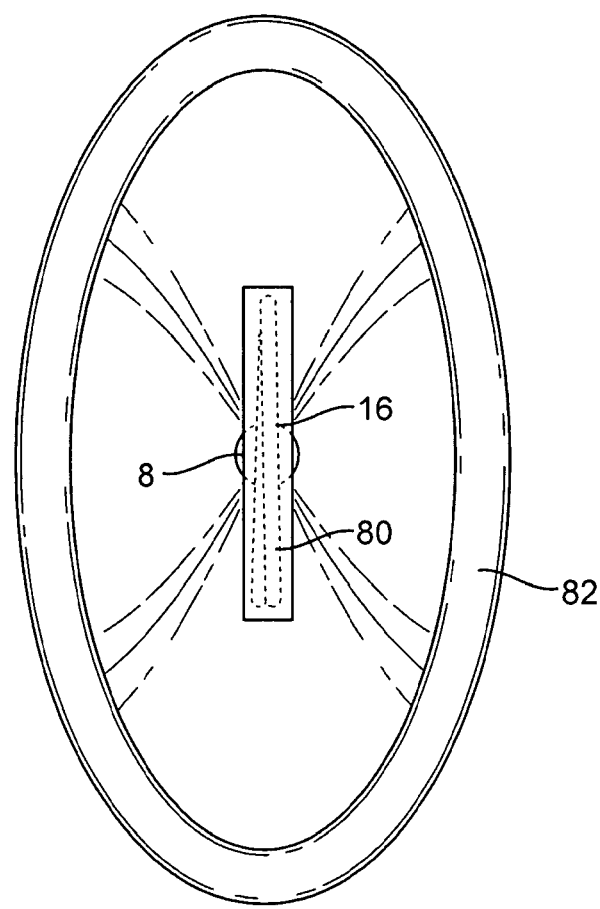
FIG. 37 is a bottom view of the container and folded drape.
Figure 38:
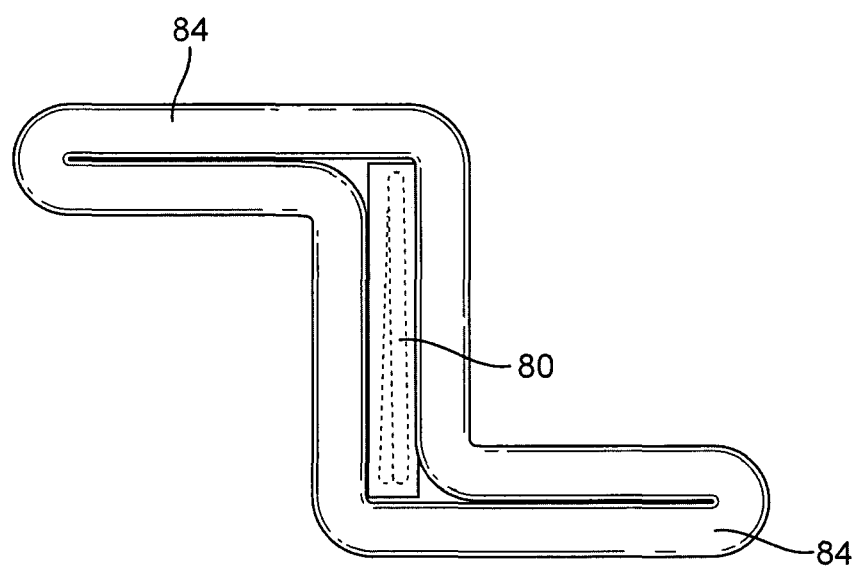
FIG. 38 shows the folded drape forming two lateral extensions.
Figure 39:
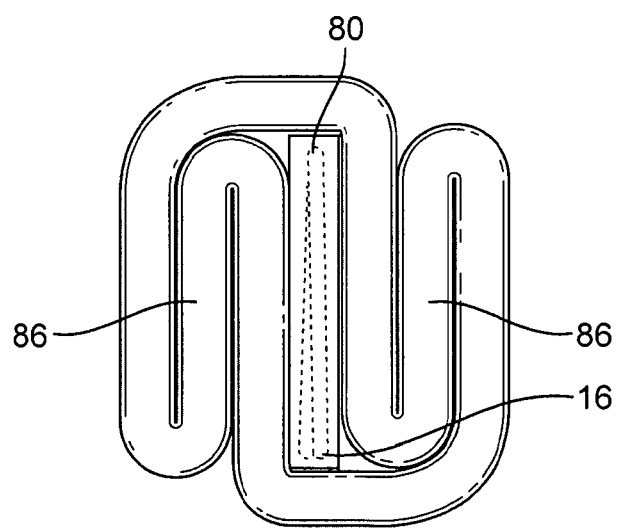
FIG. 39 shows the extensions folded to form two S-shaped sections on either side
Figure 40:
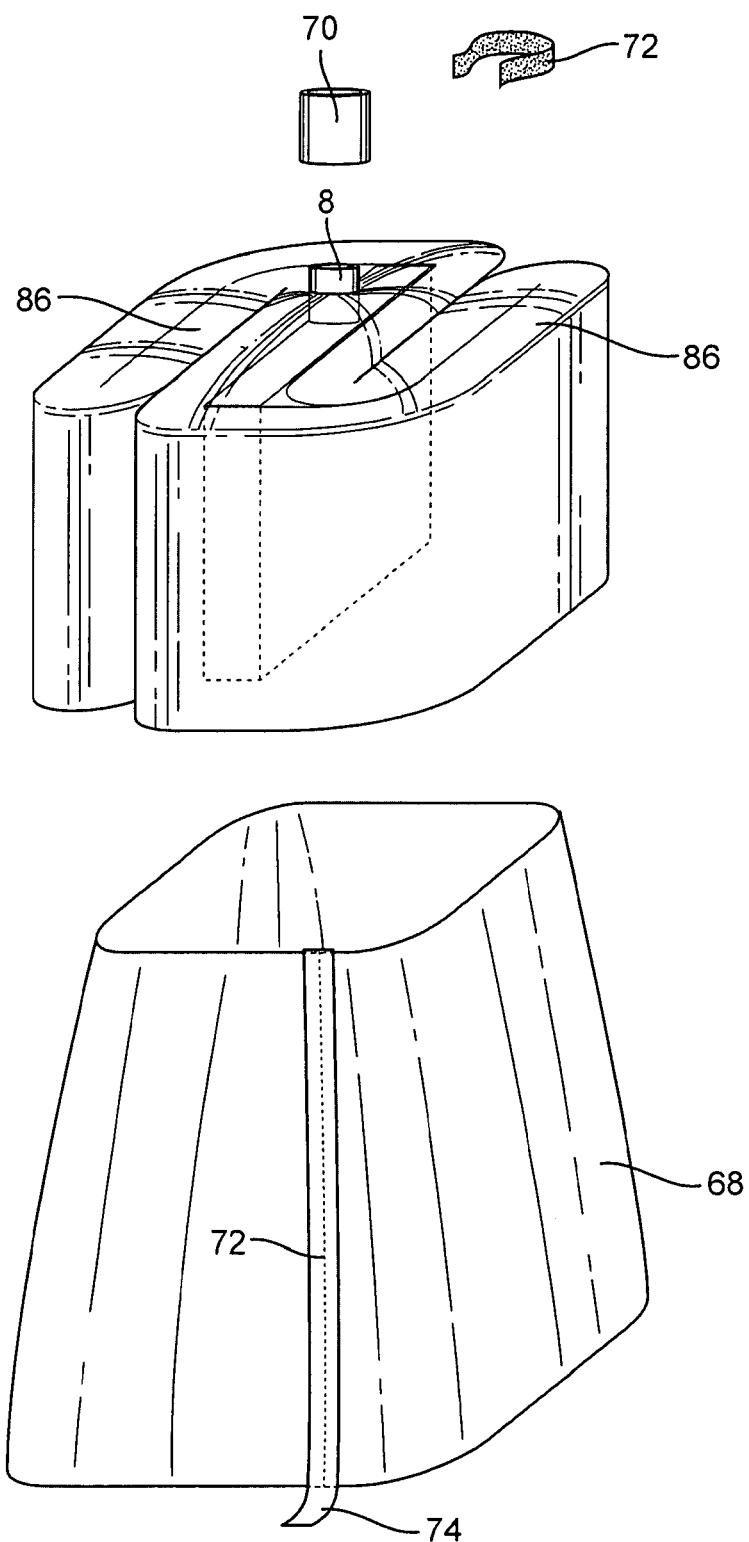
FIG. 40 shows the drape, package and package top prior to packing the drape in the package.

FIG. 33 shows the expandable element 16 held by the holder 80 with the sheath 7B and sidewall 4B of the drape 2B extending out of the holder 80. The drape 2B is then folded or cuffed in sections 82 until the cuffed sections 82 extend around the holder 80 as shown in FIG. 34-36. Referring to FIG. 37, a bottom view of the holder 80 and cuffed sheath 7B and sidewall 4B is shown. The drape 2B is then further collapsed by forming lateral extensions 84 which are folded back to form generally S-shaped portions 86 on both sides of the holder 80. The drape 2B is then ready to be placed into the package 68 and the tape 72 is applied to seal the package top 70 around the coupling 8.

Figure 41:
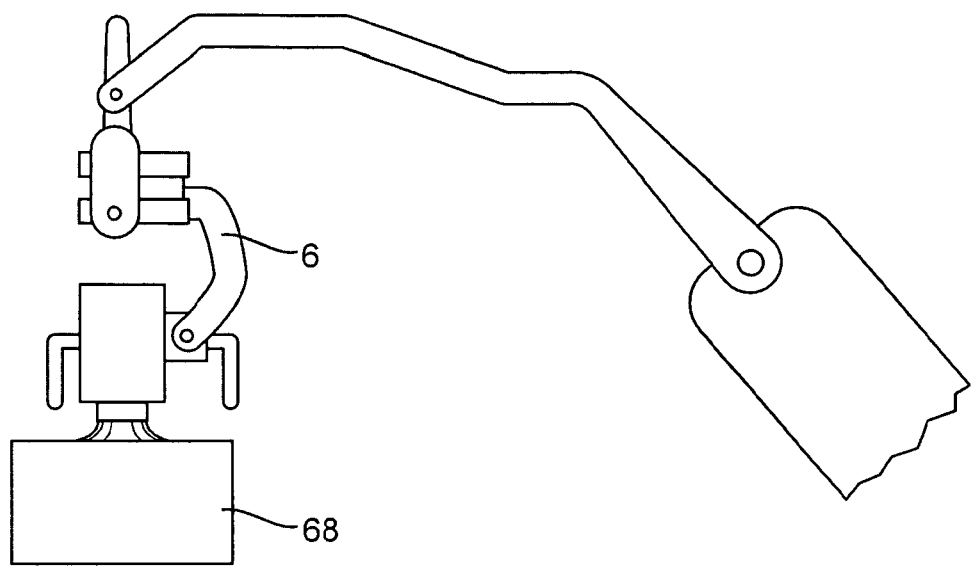
FIG. 41 shows the package coupled to the equipment.

Use of the drape 2B is now described. The package top 70 is removed from the package 68 to expose the coupling 8. The coupling 8 is then attached to the equipment 6 either directly or with the adapter 10 as described above and incorporated here and shown in FIG. 41. The drape 2B may be maintained in this position outside the sterile field since the package 68 protects the sterile side of the drape 2B.

Figure 42:
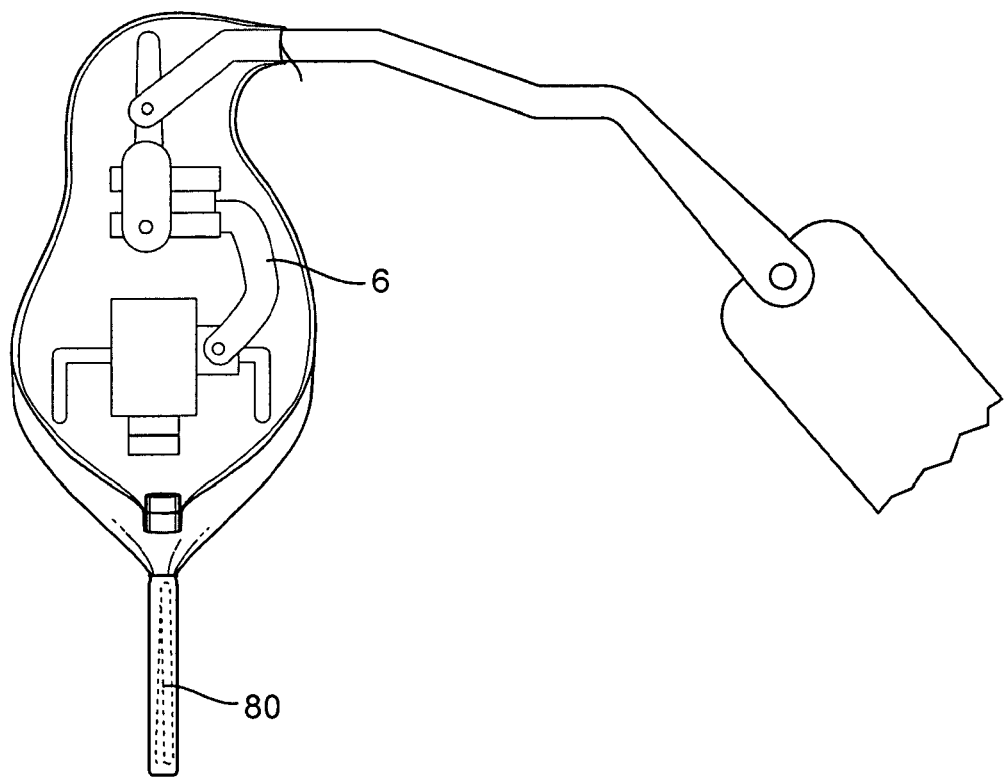
FIG. 42 shows the drape partially deployed.

The drape 2B may be further deployed outside the sterile field as shown in FIG. 42 which represents another partially deployed position. The partially deployed position of FIG. 42 is similar to the partially deployed position for the drape 2 of FIG. 18 when the drape 2 is used with the package 68. When the drape 2A is substituted for drape 2B, the drape 2B may be partially deployed as shown in FIG. 23.

The drape 2B may be completely deployed over the equipment 6 (to the fully deployed state of FIG. 25) and the container 80 removed since the sheath 7B extends over the entire sidewall 4B and coupling 8. The sheath 7B includes a tear away bond 60B which forms a seal 62B that seals the sheath 7B to the sidewall 4B to further protect the sterile outer surface 12B of the sidewall 4B. The cinches 36 are applied as the drape 2B is deployed. The drape 2B may be stored in a non-sterile area and by non-sterile personnel since the sheath covers the entire drape 2B. The sheath 7B is removed just prior to moving the equipment 6 into the sterile field.

The present invention has been described with reference to specific preferred embodiments, however, it is understood that numerous modifications may be made without departing from the scope of the invention. For example, the sheath may include a longitudinal perforation which permits removal of the sheath, the sidewall may be L-shaped and the sheath and sidewall may be sealed together using a light adhesive to protect the sterile outer surface of the sidewall all without departing from the scope of the invention.

I claim:

1. A drape for covering medical equipment comprising:
    a sidewall extending between a proximal end and a distal end defining a length;
    the sidewall being made of flexible material and having a tube shape defining a lumen for receiving the medical equipment; the tube shape having an inner surface and an outer surface; the sidewall having an opening at the distal end and a closed proximal end; the sidewall having at least one removable portion of the sidewall;
    a coupling connected near the proximal end of the sidewall; the coupling having a portion for connecting directly to medical equipment;
    one or more cinch connected to the sidewall; and
    a holder connected to the distal end of the sidewall; the holder being configured to open the distal end of the sidewall.

2. The drape of claim 1 wherein each cinch has an actuator exposed from the inner surface of the sidewall.

3. The drape of claim 1 wherein a first cinch is located near the distal end and a second cinch is located near the midpoint of the length of the sidewall.

4. The drape of claim 1 wherein the holder is movable between a collapsed configuration and an expanded configuration.

5. The drape of claim 1 wherein the holder is expandable.

6. The drape of claim 1 wherein the holder extends around at least a portion of the perimeter of the sidewall.

7. The drape of claim 1 wherein the at least one removable portion is configured for manipulating the drape in a non-sterile manner.

8. The drape of claim 1 wherein the at least one removable portion of the sidewall includes at least one handle.

9. The drape of claim 1 wherein the at least one removable portion of the sidewall is bounded by perforations.

10. A drape for covering medical equipment comprising:
    a sidewall extending between a proximal end and a distal end defining a length;
    the sidewall being made of flexible material and having a tube shape defining a lumen for receiving the medical equipment; the tube shape having an inner surface and an outer surface; the sidewall having an opening at the distal end and a closed proximal end;
    a coupling connected to the proximal end of the sidewall; the coupling having a portion for connecting directly to the medical equipment;
    a holder connected to the distal end of the sidewall; the holder being configured to open the distal end of the sidewall;
    a container removably connected to the drape such that the portion of the coupling for connecting to medical equipment is exposed while the sidewall and holder are in the container.

11. The drape of claim 10 wherein the container has an upper chamber and a lower chamber separated by a divider; wherein the holder is expandable having a collapsed configuration and an expanded configuration; the lower chamber being sized and configured to hold the holder in the collapsed configuration; and the upper chamber being sized and configured to hold the entire sidewall.

12. The drape of claim 11 wherein the divider is a circumferential lip on the inside of the container.

13. The drape of claim 10 wherein the container includes a removable cover.

14. The drape of claim 10 further including an actuator configured to removably couple the container to the coupling.

15. The drape of claim 10 wherein the container is hinged to open and close.

16. A drape for covering medical equipment comprising:
a sidewall extending between a proximal end and a distal end defining a length;
the sidewall being made of flexible material and having a tube shape defining a lumen for receiving the medical equipment; the tube shape having an inner surface and an outer surface; the sidewall having an opening at the distal end and a closed proximal end;
a coupling connected to the proximal end of the sidewall; the coupling having a portion for connecting directly to the medical equipment;
a holder connected to the distal end of the sidewall; the holder being configured to open the distal end of the sidewall;
wherein the drape has an undeployed configuration, at least one partially deployed configuration and a fully deployed configuration in which the outer surface is exposed;
wherein when in the undeployed configuration, the sidewall and holder are contained in a container such that the outer surface is not exposed; and
wherein the drape is connectable to the medical equipment when in the undeployed configuration.

17. The drape of claim 16 wherein when in the partially deployed configuration, the sidewall defines an everted configuration defining a fold such that the outer surface faces itself and the inner surface is outwardly exposed.

18. The drape of claim 17 wherein the holder is located in a container when in the partially deployed configuration.

* * * * *